United States Patent
Pringle et al.

(10) Patent No.: US 11,133,164 B2
(45) Date of Patent: **\*Sep. 28, 2021**

(54) CAPACITIVELY COUPLED REIMS TECHNIQUE AND OPTICALLY TRANSPARENT COUNTER ELECTRODE

(71) Applicant: Micromass UK Limited, Wilmslow (GB)

(72) Inventors: Steven Derek Pringle, Darwen (GB); Lajos Godorhazy, Erd (HU); Daniel Simon, Morichida (HU); Daniel Szalay, Budapest (HU); Zoltan Takats, Cambridge (GB); Tamas Karancsi, Budapest (HU)

(73) Assignee: Micromass UK Limited, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,423

(22) Filed: Jan. 31, 2020

(65) Prior Publication Data

US 2020/0168445 A1 May 28, 2020

Related U.S. Application Data

(63) Continuation of application No. 15/764,791, filed as application No. PCT/GB2016/052956 on Sep. 22, 2016.

(30) Foreign Application Priority Data

Sep. 29, 2015 (GB) .................................... 1517195

(51) Int. Cl.
*H01J 49/04* (2006.01)
*G01N 33/483* (2006.01)
(Continued)

(52) U.S. Cl.
CPC ............ *H01J 49/049* (2013.01); *G01N 21/31* (2013.01); *G01N 21/65* (2013.01);
(Continued)

(58) Field of Classification Search
CPC .. H01J 49/049; H01J 49/0459; H01J 49/0445; H01J 49/105; H01J 49/168; G01N 33/4833; G01N 21/31; G01N 21/65
See application file for complete search history.

(56) References Cited

U.S. PATENT DOCUMENTS

| 3,479,545 A | 11/1969 | Wilson |
| 3,770,954 A | 11/1973 | Davis |
(Continued)

FOREIGN PATENT DOCUMENTS

| CA | 2527886 A1 | 12/2004 |
| CA | 2876731 A1 | 12/2013 |
(Continued)

OTHER PUBLICATIONS

Shin, Y-S., et al., "Desorption Electrospray Ionization-Mass Spectrometry of Proteins" Analytical Chemistry 79:3514:3518 (2007).
(Continued)

*Primary Examiner* — Sean M Luck
(74) *Attorney, Agent, or Firm* — Kacvinsky Daisak Bluni PLLC

(57) ABSTRACT

A method of analysis is disclosed comprising providing a sample on an insulating substrate such as a petri dish 4 and contacting e.g. the rear surface of the insulating substrate with a first electrode 9. The method further comprises contacting the sample with a second electrode 2 and applying an AC or RF voltage to the first and second electrodes 9,2 in order to generate an aerosol from the sample.

20 Claims, 5 Drawing Sheets

(51) Int. Cl.
*G01N 21/31* (2006.01)
*G01N 21/65* (2006.01)

(52) U.S. Cl.
CPC ...... *G01N 33/4833* (2013.01); *H01J 49/0445* (2013.01); *H01J 49/0459* (2013.01)

(56) References Cited

U.S. PATENT DOCUMENTS

| | | | |
|---|---|---|---|
| H414 H | 1/1988 | Young et al. | |
| 4,835,383 A | 5/1989 | Mahoney et al. | |
| 4,845,367 A | 7/1989 | Amirav et al. | |
| 4,883,958 A | 11/1989 | Vestal | |
| 4,935,624 A | 6/1990 | Henion et al. | |
| 5,033,541 A | 7/1991 | D'Silva | |
| 5,053,343 A | 10/1991 | Vora et al. | |
| 5,257,991 A | 11/1993 | Fletcher et al. | |
| 5,308,977 A * | 5/1994 | Oishi | H01J 49/105 250/281 |
| 5,374,755 A | 12/1994 | Neue et al. | |
| 5,454,274 A | 10/1995 | Zhu | |
| 5,509,916 A | 4/1996 | Taylor | |
| 5,559,326 A | 9/1996 | Goodley et al. | |
| 5,800,597 A | 9/1998 | Perrotta et al. | |
| 5,828,062 A * | 10/1998 | Jarrell | H01J 49/165 250/288 |
| 5,830,214 A | 11/1998 | Flom et al. | |
| 5,836,909 A | 11/1998 | Cosmescu | |
| 5,969,352 A | 10/1999 | French et al. | |
| 5,989,015 A | 11/1999 | Guerin et al. | |
| 6,032,673 A | 3/2000 | Savage et al. | |
| 6,333,632 B1 * | 12/2001 | Yang | G01N 27/70 324/459 |
| 6,348,688 B1 | 2/2002 | Vestal | |
| 6,825,464 B2 | 11/2004 | De La Mara | |
| 6,998,622 B1 | 2/2006 | Wang et al. | |
| 7,238,936 B2 | 7/2007 | Okamura et al. | |
| 7,247,845 B1 | 7/2007 | Gebhardt et al. | |
| 7,329,253 B2 | 2/2008 | Braunstein et al. | |
| 7,335,897 B2 | 2/2008 | Takats et al. | |
| 7,365,309 B2 | 4/2008 | Denny et al. | |
| 7,517,348 B2 | 4/2009 | Vetter et al. | |
| 7,564,028 B2 | 7/2009 | Vestal | |
| 7,718,958 B2 | 5/2010 | Shiea et al. | |
| 7,828,948 B1 | 11/2010 | Hatch et al. | |
| 7,960,711 B1 | 6/2011 | Sheehan et al. | |
| 8,156,151 B2 | 4/2012 | Sidman | |
| 8,193,487 B2 | 6/2012 | Briglin et al. | |
| 8,232,520 B2 | 7/2012 | Cristoni | |
| 8,253,098 B2 | 8/2012 | Hiraoka et al. | |
| 8,286,260 B2 | 10/2012 | Vertes et al. | |
| 8,314,382 B2 | 11/2012 | Takats | |
| 8,334,504 B2 | 12/2012 | Finlay et al. | |
| 8,431,409 B1 | 4/2013 | Meinhart et al. | |
| 8,448,493 B2 | 5/2013 | McIntyre et al. | |
| 8,481,922 B2 | 7/2013 | Musselman | |
| 8,778,695 B2 | 7/2014 | Caprioli | |
| 8,803,085 B2 | 8/2014 | Ouyang et al. | |
| 8,834,462 B2 | 9/2014 | Johnson et al. | |
| 8,970,840 B2 * | 3/2015 | Kulkarni | G01N 15/06 356/313 |
| 9,046,448 B2 | 6/2015 | Takats | |
| 9,053,914 B2 | 6/2015 | Pringle et al. | |
| 9,082,603 B2 | 7/2015 | Bajic | |
| 9,120,083 B2 | 9/2015 | Wyndham et al. | |
| 9,255,907 B2 | 2/2016 | Heanue et al. | |
| 9,281,174 B2 | 3/2016 | Takats | |
| 9,287,100 B2 | 3/2016 | Szalay et al. | |
| 9,709,529 B2 | 7/2017 | Takats | |
| 9,731,219 B2 | 8/2017 | Wang et al. | |
| 9,947,524 B2 | 4/2018 | Pringle et al. | |
| 10,186,626 B2 | 1/2019 | Song et al. | |
| 2002/0008871 A1 | 1/2002 | Poustka et al. | |
| 2002/0070338 A1 | 6/2002 | Loboda | |
| 2002/0076824 A1 | 6/2002 | Haglund, Jr. et al. | |
| 2003/0001084 A1 | 1/2003 | Bateman et al. | |
| 2003/0008404 A1 | 1/2003 | Tomita et al. | |
| 2003/0015657 A1 * | 1/2003 | Takada | H01J 49/0445 250/288 |
| 2003/0042412 A1 | 3/2003 | Park | |
| 2003/0080278 A1 | 5/2003 | Okada et al. | |
| 2003/0119193 A1 | 6/2003 | Hess et al. | |
| 2003/0135222 A1 | 7/2003 | Baska | |
| 2003/0136918 A1 * | 7/2003 | Hartley | H01J 49/168 250/423 R |
| 2003/0193023 A1 | 10/2003 | Marsh | |
| 2004/0007673 A1 | 1/2004 | Coon et al. | |
| 2004/0079881 A1 * | 4/2004 | Fischer | H01J 49/162 250/288 |
| 2004/0124352 A1 | 7/2004 | Kashima et al. | |
| 2004/0197899 A1 | 10/2004 | Gomez et al. | |
| 2004/0217274 A1 | 11/2004 | Bai et al. | |
| 2004/0235395 A1 | 11/2004 | Hashish et al. | |
| 2005/0017091 A1 | 1/2005 | Olsen et al. | |
| 2005/0032471 A1 | 2/2005 | Pfarr et al. | |
| 2005/0061779 A1 | 3/2005 | Blumenfeld et al. | |
| 2005/0067565 A1 | 3/2005 | Takada et al. | |
| 2005/0072916 A1 | 4/2005 | Park | |
| 2005/0074361 A1 | 4/2005 | Tanoshima et al. | |
| 2005/0077644 A1 | 4/2005 | Bryan et al. | |
| 2005/0124986 A1 | 6/2005 | Braunstein et al. | |
| 2005/0138861 A1 | 6/2005 | O'Connor | |
| 2005/0154490 A1 | 7/2005 | Blaine et al. | |
| 2005/0159765 A1 | 7/2005 | Moutafis et al. | |
| 2005/0178962 A1 | 8/2005 | Guevremont et al. | |
| 2005/0178975 A1 | 8/2005 | Glukhoy | |
| 2005/0230634 A1 | 10/2005 | Bajic et al. | |
| 2005/0230635 A1 | 10/2005 | Takats et al. | |
| 2005/0258358 A1 | 11/2005 | Thakur | |
| 2005/0269518 A1 | 12/2005 | Bajic et al. | |
| 2005/0274885 A1 | 12/2005 | Brown et al. | |
| 2006/0035570 A1 | 2/2006 | Chisum et al. | |
| 2006/0054806 A1 * | 3/2006 | Yamada | H01J 49/168 250/288 |
| 2006/0091308 A1 | 5/2006 | Boyle et al. | |
| 2006/0097084 A1 | 5/2006 | Gromer et al. | |
| 2006/0108539 A1 | 5/2006 | Franzen | |
| 2006/0122593 A1 | 6/2006 | Jun | |
| 2006/0138321 A1 | 6/2006 | Ahern et al. | |
| 2006/0145089 A1 | 7/2006 | Cristoni et al. | |
| 2006/0186334 A1 | 8/2006 | Jolliffe et al. | |
| 2006/0250138 A1 | 11/2006 | Sparkman et al. | |
| 2006/0255264 A1 | 11/2006 | Belford | |
| 2007/0023631 A1 | 2/2007 | Takats et al. | |
| 2007/0023677 A1 | 2/2007 | Perkins et al. | |
| 2007/0094389 A1 | 4/2007 | Nussey et al. | |
| 2007/0114394 A1 | 5/2007 | Combs et al. | |
| 2007/0114437 A1 | 5/2007 | Kovtoun | |
| 2007/0176113 A1 | 8/2007 | Shiea et al. | |
| 2007/0181802 A1 | 8/2007 | Yamada et al. | |
| 2008/0001081 A1 | 1/2008 | Jindai et al. | |
| 2008/0042056 A1 | 2/2008 | Fischer et al. | |
| 2008/0067352 A1 | 3/2008 | Wang | |
| 2008/0073503 A1 | 3/2008 | Wu | |
| 2008/0073512 A1 | 3/2008 | Siuzdak et al. | |
| 2008/0149822 A1 | 6/2008 | Vertes et al. | |
| 2008/0172075 A1 | 7/2008 | Ammann | |
| 2008/0173809 A1 | 7/2008 | Wu | |
| 2008/0234579 A1 | 9/2008 | Halevy-Politch et al. | |
| 2008/0312651 A1 | 12/2008 | Pope et al. | |
| 2009/0065714 A1 | 3/2009 | Keady | |
| 2009/0082637 A1 | 3/2009 | Galperin | |
| 2009/0126891 A1 | 5/2009 | Koivunen et al. | |
| 2009/0159790 A1 | 6/2009 | Kostiainen et al. | |
| 2009/0272893 A1 | 11/2009 | Hieftje et al. | |
| 2009/0302211 A1 | 12/2009 | Takats | |
| 2010/0012830 A1 | 1/2010 | Cristoni | |
| 2010/0072359 A1 | 3/2010 | Briglin et al. | |
| 2010/0078550 A1 | 4/2010 | Wiseman et al. | |
| 2010/0101304 A1 | 4/2010 | McIntyre et al. | |
| 2010/0176290 A1 | 7/2010 | Vidal-de-Miguel | |
| 2010/0186524 A1 | 7/2010 | Ariessohn et al. | |
| 2010/0229263 A1 | 9/2010 | Vertes et al. | |
| 2011/0036978 A1 | 2/2011 | Franzen | |

(56) References Cited

U.S. PATENT DOCUMENTS

| | | |
|---|---|---|
| 2011/0049352 A1 | 3/2011 | Ding et al. |
| 2011/0059554 A1 | 3/2011 | Albers et al. |
| 2011/0066147 A1 | 3/2011 | He et al. |
| 2011/0087308 A1 | 4/2011 | Morgan et al. |
| 2011/0295250 A1 | 12/2011 | Johnson et al. |
| 2012/0018628 A1 | 1/2012 | Wuijckhuijse et al. |
| 2012/0043460 A1 | 2/2012 | Wouters et al. |
| 2012/0048264 A1 | 3/2012 | Finlay et al. |
| 2012/0074306 A1 | 3/2012 | Jesse et al. |
| 2012/0079894 A1 | 4/2012 | Van Berkel et al. |
| 2012/0080592 A1 | 4/2012 | Wiseman et al. |
| 2012/0085649 A1* | 4/2012 | Sano ............... B01L 3/502715 204/547 |
| 2012/0119079 A1 | 5/2012 | Ouyang et al. |
| 2012/0149009 A1 | 6/2012 | Levis et al. |
| 2012/0156712 A1 | 6/2012 | Takats |
| 2012/0295276 A1 | 11/2012 | Cooks et al. |
| 2013/0178845 A1 | 7/2013 | Smith et al. |
| 2013/0181126 A1 | 7/2013 | Jong |
| 2013/0303846 A1 | 11/2013 | Cybulski et al. |
| 2014/0151547 A1 | 6/2014 | Bajic |
| 2014/0276775 A1 | 9/2014 | Funk et al. |
| 2014/0291506 A1 | 10/2014 | Tikhonski et al. |
| 2014/0297201 A1 | 10/2014 | Knorr et al. |
| 2014/0299577 A1 | 10/2014 | Chung et al. |
| 2014/0326865 A1 | 11/2014 | Pringle et al. |
| 2014/0353488 A1 | 12/2014 | Takats |
| 2014/0353489 A1 | 12/2014 | Szalay et al. |
| 2015/0021469 A1 | 1/2015 | Bajic |
| 2015/0048255 A1 | 2/2015 | Jarrell |
| 2015/0087003 A1 | 3/2015 | Charles et al. |
| 2015/0144782 A1 | 5/2015 | Fogwill et al. |
| 2015/0192590 A1 | 7/2015 | Sodeoka et al. |
| 2015/0201913 A1 | 7/2015 | Takats |
| 2016/0002696 A1 | 1/2016 | Galiano |
| 2016/0133450 A1 | 5/2016 | Green et al. |
| 2016/0215322 A1 | 7/2016 | Goodlett et al. |
| 2016/0247668 A1 | 8/2016 | Szalay et al. |
| 2016/0341712 A1 | 11/2016 | Agar |
| 2016/0372313 A1 | 12/2016 | Brown et al. |
| 2017/0103880 A1 | 4/2017 | Syage |
| 2018/0136091 A1 | 5/2018 | Ryan et al. |

FOREIGN PATENT DOCUMENTS

| | | |
|---|---|---|
| CA | 2882003 A1 | 2/2014 |
| CN | 101073137 A | 11/2007 |
| CN | 101170043 A | 4/2008 |
| CN | 101288146 A | 10/2008 |
| CN | 101413905 A | 4/2009 |
| CN | 101490524 A | 7/2009 |
| CN | 201266145 Y | 7/2009 |
| CN | 101657158 A | 2/2010 |
| CN | 101871914 A | 10/2010 |
| CN | 102026709 A | 4/2011 |
| CN | 102137618 A | 7/2011 |
| CN | 102164675 A | 8/2011 |
| CN | 102264404 A | 11/2011 |
| CN | 102445544 A | 5/2012 |
| CN | 102483369 A | 5/2012 |
| CN | 102800553 A | 11/2012 |
| CN | 102879453 A | 1/2013 |
| CN | 102928610 A | 2/2013 |
| CN | 103295873 A | 9/2013 |
| CN | 103597574 A | 2/2014 |
| CN | 104062348 A | 9/2014 |
| CN | 104254772 A | 12/2014 |
| CN | 104254901 A | 12/2014 |
| EP | 0169469 A2 | 1/1986 |
| EP | 0437358 A2 | 7/1991 |
| EP | 1855306 A1 | 11/2007 |
| EP | 3265817 A1 | 1/2018 |
| EP | 3266035 A1 | 1/2018 |
| GB | 2425178 A | 10/2006 |
| GB | 2491486 A | 12/2012 |
| JP | S63243864 A | 10/1988 |
| JP | 03001435 A | 1/1991 |
| JP | H0785834 A | 3/1995 |
| JP | H07130325 A | 5/1995 |
| JP | H10247472 A | 9/1998 |
| JP | H10302710 A | 11/1998 |
| JP | 2000180413 A | 6/2000 |
| JP | 2001183345 A | 7/2001 |
| JP | 2002170518 A | 6/2002 |
| JP | 2004264043 A | 9/2004 |
| JP | 2005205181 A | 8/2005 |
| JP | 2006329710 A | 12/2006 |
| JP | 2007051934 A | 3/2007 |
| JP | 2007170870 A | 7/2007 |
| JP | 2007218916 A | 8/2007 |
| JP | 2010169454 A | 8/2010 |
| JP | 2014515831 A | 7/2014 |
| JP | 2015503109 A | 1/2015 |
| JP | 2015504160 A | 2/2015 |
| KR | 1020020013544 A | 4/2007 |
| KR | 1020100106336 A | 10/2010 |
| WO | 9734534 A1 | 9/1997 |
| WO | 0160265 A1 | 8/2001 |
| WO | 2008148557 A2 | 12/2008 |
| WO | 2010075265 A2 | 7/2010 |
| WO | 2010136887 A1 | 12/2010 |
| WO | 2011114902 A1 | 9/2011 |
| WO | 2012143737 A1 | 10/2012 |
| WO | 2012164312 A2 | 12/2012 |
| WO | 2012174437 A1 | 12/2012 |
| WO | 2013098642 A2 | 7/2013 |
| WO | 2013098645 A2 | 7/2013 |
| WO | 2013102670 A1 | 7/2013 |
| WO | 2013148162 A1 | 10/2013 |
| WO | 2014106165 A | 7/2014 |
| WO | 2014128629 A1 | 8/2014 |
| WO | 2014140601 A1 | 9/2014 |
| WO | 2014142926 A1 | 9/2014 |
| WO | 2014202828 A1 | 12/2014 |
| WO | 2015004457 A1 | 1/2015 |
| WO | 2015132579 A1 | 9/2015 |
| WO | 2016046748 A1 | 3/2016 |
| WO | 2016142674 A1 | 9/2016 |
| WO | 2016156615 A1 | 10/2016 |

OTHER PUBLICATIONS

Waters DESI System Operators Guide 715004701/Revision A, Waters Corporation, [online] Jan. 2015 [retrieved on Dec. 3, 2020].

Chen, X., ed., "Liquid Chromatography-Mass Spectrometry—Chapter 8", in Principle and Application of Chromatographic Analysis Technology, Chinese Peoples Public Security University Press, (Jan. 2014) 6 pages.

Song, Y., et al., "Rapid ambient mass spetrometric profiling of intact, untreated bacteria using desoprtion electrospray ionization" ChemComm pp. 61-63 (2007).

Wiseman, J.M. and Li, J.B., "Elution, Partial Separation, and Identification of Lipids Directly from Tissue Slices on Planar Chromatogrpahy Media by Desoprtion Electrospray Ionization Mass Spectrometry", Anal Chem 82:8866-8874 (2010).

Krouskop, T., et al., "Elastic moduli of breast and prostate tissues under compression" Ultrasonic Imaging 20:260-274 (1998).

Aberg, P., et al., "Skin Cancer Identification Using Multifrequency Electrical Impedance—A Potential Screening Tool", IEEE Transactions on Biomedical Engineering, 51(12): 2097-2102 (2004).

Examination Report under Section 18(3) for Application No: GB2015580.0, dated Jan. 21, 2021, 4 pages.

Rath, C.M., et al., "Molecular Analysis of Model Gut Microbiotas by Imaging Mass Spectrometry and Nanodesorption Electrospray Ionization Reveals Dietary Metabolite Tranformations" Analytical Chemistry 84(21):9259-9267 (2012).

Fenselau, C.C., "Rapid Characterization of Microorganisms by Mass Spectrometry—What Can Be Learned and how?" Journal of the American Society for Mass Spectrometry 24(8):1161-1166 (2013).

(56) References Cited

OTHER PUBLICATIONS

Uetrecht, C. et al., "Modern Biomolecular Mass Spectrometry and its Role in Studying Virus Structure, Dynamics and Assembly" Angewandte Chemie International Edition 50(36):8248-8262 (2011).
Forbes, T.P. et al., "Chemical imaging of artificial Fingerprints by desorption electro-flow focusing ionization mass spectrometry" Analyst 139(12):2982-2985 (2014).
Cornett, D. S., et al, "A Novel Histology-directed Strategy for MALDI-MS Tissue Profiling That Improves Throughput and Cellular Specificity in Human Breast Cancer", American Society for Biochemistry and Molecular Biology, p. 1975-1983, Jul. 18, 2006.
Summons to Attend Oral Proceedings Pursuant to Rule 115(1) EPC of EP Application No. 12726643.5, dated Apr. 20, 2018, 7 pages.
Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.
Agar, N. et al., "Development of Stereotactic Mass Spectrometry for Brain Tumor Surgery", Biosis, Neurosurgery [online], vol. 68, No. 2, (Feb. 2011) pp. 280-290.
Ahlf, Dorothy R. et al., "Correlated Mass Spectrometry Imaging and Confocal Raman Microscopy for Studies of Three-Dimensional Cell Culture Sections", Analyst, vol. 139, No. 18, p. 4578 (2014).
Azimzadeh, Omid et al., "Formalin-Fixed Paraffin-Embedded (FFPE) Proteome Analysis Using Gel-Free and Gel-Based Proteomics", Journal of Proteome Research, vol. 9, No. 9, pp. 4710-4720 (2010).
Balgley, Brian M. et al., "Evaluation of Archival Time on Shotgun Proteomics of Formalin-Fixed and Paraffin-Embedded Tissues", Journal of Proteome Research, vol. 8 No. 2, pp. 917-925 (2009).
Balog, Julia et al., "Identification of Biological Tissues by Rapid Evaporative Ionization Mass Spectrometry", Analytical Chemistry, vol. 82, No. 17, pp. 7343-7350 (Sep. 2010).
Balog, Julia et al., "Supporting Information for Identification of Biological Tissues by Rapid Evaporative Ionization Mass Spectrometry", pp. SI-S9, http://pubs.acs.org/doi/suppl/10.1021/ac101, (2013).
Balog, J. et al., "Intraoperative Tissue Identification Using Rapid Evaporative Ionization Mass Spectrometry", Science Translational Medicine, vol. 5, No. 194, pp. 1-11 (Jul. 2013).
Balog, J. et al., "Supplementary Materials: Intraoperative Tissue Identification Using Rapid Evaporative Ionization Mass Spectrometry", Science Translational Medicine, vol. 5, No. 194 34 pages (Jul. 2013).
Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B: Biomedical Sciences Applications, Elsevier, Amersterdam, NL, vol. 901, pp. 41-46 (May 2012).
Bellet, V. et al., "Proteomic Analysis of RCL2 Paraffin-Embedded Tissues", Journal of Cellular and Molecular Medicine, vol. 12, No. 5B, pp. 2027-2036 (2008).
Bocklitz, T.W. et al., "Deeper Understanding of Biological Tissue: Quantitative Correlation of MALDITOF and Raman Imaging", Analytical Chemistry, vol. 85 No. 22, pp. 10829-10834 (2013).
Chen, H., et al: "Neutral desorption sampling coupled to extractive electrospray ionization mass spectrometry for rapid differentiation of biosamples by metabolomic fingerprinting", Journal of Mass Spectromety, vol. 42, No. 9, Sep. 1, 2007 pp. 1123-1135.
Cole, Laura M. et al., "Mass Spectrometry Imaging for the Proteomic Study of Clinical Tissue", Proteomics—Clinical Applications, vol. 9, No. 3-4, pp. 335-341 (Apr. 2015).
Crawshaw, Benjamin et al., "Gastrointestinal Surgery: Real-Time Tissue Identification During Surgery", Nature Review/Gastroenterology Hepatology, vol. 10, No. 11. pp. 624-625.
Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers in Surgery and Medicine, vol. 44, No. 5, pp. 406-412 (Jul. 2012).

Davies, T.J. et al., "Volatile Products from Acetylcholine as Markers in the Rapid Urine Test Using Head-Space Gas-Liquid Chromatography",Journal of Chromatography B: Biomedical Sciences and Application, vol. 307, pp. 11-21 (Jan. 1984).
European Commission, "ISD Report Summary", http://cordis.europa.eu/result/rcn/163435_e, (2016).
Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).
Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (Mar. 2012).
Golf, Ottmar et al., "Rapid Evaporative Ionization Mass Spectrometry Imaging Platform for Direct Mapping from Bulk Tissue and Bacterial Growth Media", Analytical Chemistry, vol. 87, No. 5, pp. 2527-2534 (Mar. 2015).
Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (Nov. 2014).
Guenther, Sabine et al., "Electrospray Post-Ionization Mass Spectrometry of Electrosurgical Aerosols", Journal of The American Society for Mass Spectrometry, vol. 22, No. 11, pp. 2082-2089 (Nov. 2011).
Gustafsson, Ove J.R. et al., "Proteomic Developments in the Analysis of Formalin-Fixed Tissue", Biochimica et Biophysica Acta, vol. 1854, No. 6, pp. 559-580.
Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998.
Hobbs, S.K. et al.,"Magnetic Resonance Image-Guided Proteomics of Human Glioblastoma Multiforme", Journal of Magnetic Resonance Imaging, vol. 18, pp. 530-536 (Jan. 2003).
Hsu, C. et al., "Visualizing Life with Ambient Mass Spectrometry", Current Opinion in Biotechnology, vol. 31, pp. 24-34 (2015).
Jadoul, L. et al., "Matrix-Assisted Laser Desorption/Ionization Mass Spectrometry and Raman Spectroscopy: An Interesting Complementary Approach for Lipid Detection in Biological Tissues", Eurooean Journal of Lipid Science and Technology. vol. 116, No. 8. pp. 1080-1086 (2014).
Jain, M. et al., "Metabolite Profiling Identifies a Key Role for Glycine in Rapid Cancer Cell Proliferation", American Association for the Advancement of Science, vol. 336, No. 6084, pp. 1040-1044 (May 2012).
Jarmusch, Alan K. et al., "Detection of Strep Throat Causing Bacterium Directly from Medical Swabs by Touch Spray-Mass Spectrometry", Analyst, vol. 139, No. 19, pp. 4785 (Jan. 1, 2014).
Jarmusch, Alan K. et al., "Supplemental Information Detection of Strep Throat Causing Bacterium Directly from Medical Swabs by Touch Spray-Mass Spectrometry", http://www.rsc.org/suppdata/an/c4/c4an00959b/c4an00959b1.
Lazova, Rossitza et al., "Imaging Mass Spectrometry—A New and Promising Method to Differentiate Spitz Nevi From Spitwid Malignant Melanomas", American Journal of Dermatopathology, vol. 34, No. 1, pp. 82-90 (Feb. 2012).
Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, p. 15 (2013).
Lieuwe, D.J. et al., "Volatile Metabolites of Pathogens: A Systematic Review", PLoS Pathogens, vol. 9, Issue 5, e1003311 (May 2013).
Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (Oct. 1996).
Mccullough, Bryan J. et al., "On-Line Reaction Monitoring by Extractive Electrospray Ionisation", Rapid Communications in Mass Spectrometry, vol. 25, No. 10, pp. 1445-1451 (May 2011).

(56) References Cited

OTHER PUBLICATIONS

Moot, A. et al: "Composition of Volatile Organic Compouds in Diathermy Plume as Detected by Selected Ion Flow Tube Mass Spectrometry", ANZ Journal of Surgery, vol. 77, No. 1-2, (Jan. 2007) pp. 20-23.
Murray, Patrick R, "What Is New in Clinical Microbiology—Microbial Identification by MALDI-TOF Mass Spectrometry", Journal of Molecular Diagnostics, vol. 14, No. 5, pp. 419-423 (Sep. 2012).
Nicholson, Jeremy K. et al., "Metabolic Phenotyping in Clinical and Surgical Environments", Nature, vol. 491, No. 7424 pp. 384-392 (Nov. 2012).
Pirro, Valentina et al., "Direct Drug Analysis from Oral Fluid Using Medical Swab Touch Spray Mass Spectrometry", Analytics Chimica Acta, vol. 861, Jan. 7, 2015 pp. 47-54.
Plata, N. et al., "Aerosols Sampling Using a New Cryogenic Instrument", Journal of Aerosol Science, Pergamon, Amsterdam, NL vol. 37, No. 12, pp. 1871-1875 (Dec. 2006).
Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).
Schafer, Karl-Christian et al., "In Vivo, In Situ Tissue Analysis Using Rapid Evaporative Ionization Mass Spectrometry", Angewandte Chemie International Edition, vol. 48, No. 44, pp. 8240-8242 (Oct. 2009).
Ellis, S. et al., "Surface Analysis of Lipids by Mass Spectrometry: More Than Just Imaging", Progress in Lipid Research Pergamon Press, vol. 52, No. 4, pp. 329-353 (Oct. 2013).
Shoemaker, Robert H., "The NCI60 Human Tumour Cell Line Anticancer Drug Screen", (2013).
Strittmatter, N. et al., "Anaylsis of Intact Bacteria Using Rapid Evaporative Ionization Mass Spectrometry", Chemical Communications—Chemcon, vol. 49, No. 55, p. 6188 (May 2013).
Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (Jul. 2014 ).
Strittmatter, N. et al., "Taxon-Specific Markers for the Qualitative and Quantitative Detection of Bacteria in Human Samples", https://www.msacl.org/2015 US Long Abstract.
Strittmatter, N.: "Home—Miss Nicole Strittmatter" Retrieved from the Internet URL: http://www.imperial.ac.uk/people/n.strittmatter12 [retrieved on May 19, 2016] the whole document.
Extended European Search Report for Application No. 20210062.4, dated Mar. 9, 2021, 13 pages.
Examination Report for GB Patent Application No. GB2015580.0, dated Mar. 12, 2021.
Examination Report under Section 18(3) for Application No. GB1714165.6, dated Mar. 22, 2021, 6 pages.
Examination Report under Section 18(3) for Application No. GB1715750.4 dated Mar. 22, 2021, 5 pages.
Tait, Emma et al., "Identification of Volatile Organic Compounds Produced by Bacteria Using HS-SPME-GC-MS", Journal of Chromatographic Sci, pp. 1-11.
Uribe, D.0. et al., "Piezoelectric Self-Sensing System for Tactile Intraoperative Brain Tumor Delineation in Neurosurgery", Proceedings of the 31st Annual International Conference of the IEEE Engineering in Medicine and Biology Society: Engineering the Future of BioMedicine, IEEE pp. 737-740 (Sep. 2009).
Kohler, M. et al. "Characterization of lipid extracts from brain tissue and tumors using Raman spectroscopy and mass spectrometry," Anal Bioana Chem, 393:1513-1520, Jan. 20, 2009.
Vander Wilp, W. et al., "Lead in Micro-Samples of Whole Blood by Rhenium-Cup in-Torch Vaporization-Inductively Coupled Plasma-Atomic Emission Spectrometry (ITV-ICP-AES)", Fresenius Journal of Analytical Chemistry, vol. 368, No. 7, pp. 734-736 (Nov. 2000).
Vircks, Kyle E. et al., "Rapid Screening of Synthetic Cathinones as Trace Residues and in Authentic Seizures Using a Portable Mass Spectrometer Equipped with Desorption Electrospray Ionization", Rapid Communications in Mass Spectrometry, vol. 26, No. 23, pp. 2665-2672 (Dec. 15, 2012).
Wehofsky, et al "Automated deconvolution and deisotoping of electrospray mass spectra" J. Mass Spectrom. 2002; 37: pp. 223-229.
Al Sahaf et al., "Chemical Composition of Smoke Produced by High-Frequency Electrosurgery", Irish Journal of Medical Science, vol. 176, No. 3, pp. 229-232, 2007.
Barrett et al., "Surgical Smoke: A Review of the Literature", Surgical Endoscopy, vol. 17, No. 6, pp. 979-987, 2003.
Down, "A DESI-Rable Ionization Revolutionizes Mass Spectrometry", Base Peak, 2005.
International Search Report and Written Opinion for International Application. No. PCT/IB2012/003009, dated Aug. 14, 2013, 17 pages.
PCT International Search Report and Written Opinion for International Appln. No. PCT/IB2010/001261, dated Sep. 21, 2010, 5 pages.
PCT International Search Report and Written Opinion for International Appln. No. PCT/IB2012/002995, dated Sep. 10, 2013, 3 pages.
Qiao et al., "Electrostatic-Spray Ionization Mass Spectrometry", Analytical Chemistry, vol. 84, No. 17, pp. 7422-7430, 2012.
Lee et al., "Thermally Assisted Electrospray Interface for Liquid Chromatography/Mass Spectrometry", Rapid Communications in Mass Spectrometry, vol. 6, pp. 727-733, 1992.
McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.
Sakairi et al., "Characteristics of a Liquid Chromatograph/Atmospheric Pressure Ionization Mass Spectrometer", Anal. Chem., vol. 60, pp. 774-780, 1988.
Takats et al., "Characterization of DESI-FTICR Mass Spectrometry—From ECD to Accurate Mass Tissue Analysis", Journal of Mass Spectrometry, vol. 43, pp. 196-203, 2008.
Eagles, et al., "Fast Atom Bombardment Mass Spectrometry of Amine Mixtures", John Wiley Sons, Ltd, 1988.
Slemr et al., Concentration Profiles of Diamines in Fresh and aerobically Stored Park and Beef, American Chemical Society, 1985.
Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).
Van Berkel, "Thin-Layer Chromatography and El3ectrospray Mass Spectrometry Coupled Using a Surface Sampling probe", Anal. Chem. 2002.
Takats et al., "Mass Spectrometry Sampling Under Ambient Conditions with Desorption Electrospray Ionization", Science, vol. 306, 2004.
Tottszer et al., "Laser Heating Versus Resistive Heating in the Field-Desorption Mass Spectrometry of Organic Polymers", J. Phys. D: Appl. Phys., vol. 21, pp. 1713-1720, 1988.
Zhou, X. et al. "Development of miniature mass spectrometry systems for bioanalysis outside the conventional laboratories." Bioanalysis, 6 (11) 1497-1508 (2014).
Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).
McJimpsey, E.L., et al., "Parameters Contributing to Efficient Ion Generation in Aerosol MALDI Mass Spectrometry," American Society for Mass Spectrometry pp. 1044-0305 (2007).
Mutters, N.T., et al., "Performance of Kiestra Total Laboratory Automation Combined with MS in Clinical Microbiology Practice," Annals of Laboratory Medicine 34: 111-117 (2014).
Longuespee, R., et al., Tissue Proteomics for the Next Decade Towards a Molecular Dimension in Histology, OMICS A Journal of Integrative Biology 28(9): 539-552 (2014).

(56) References Cited

OTHER PUBLICATIONS

Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).

Suarez, S. et al., Ribosomal proteins as biomarkers for bacterial identification by mass spectrometry in the clinical microbiology laboratory, Journal of microbiological Methods, 94: 390-396 (2013).

Trimpin, S. et al., New Ionization Method for Analysis on Atmospheric Pressure Ionization Mass Spectrometers Requiring Only Vacuum and Matrix Assistance, Analytical Chemistry, 85:2005-2009 (2013).

Cha, S., Laser desorption/ionization mass spectrometry for direct profiling and imaging of small moledcules from raw biological materials, Doctoral Dissertation, Iowa State University (2008).

Asano et al., "Self-aspirating atmospheric pressure chemical ionization source for direct sampling of analytes on Surfaces in liquid solution", Rapid Communications in Mass Spectrometry 2005.

International Search Report and Written Opinion for application No. PCT/GB2017/051050, dated Jun. 27, 2017, 15 pages.

Gerbig, Stefanie et al, "Spatially resolved investigation of systemic and contact pesticides in plant material by desorption electrospray ionization mass spectrometry imagine", Analytical and Bioanalytical Chemistry, 407(24):7379-7389 (2015).

Lesiak, A., et al.,"Rapid detection by direct analysis in real time-mass spectrometry (DART-MS) of psychoactive plant drugs of abuse: the case of Mitragyna speciosa aka "Kratom"", 242:210-218 (2014).

Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).

Nielen, M et la., "Desorption electrospray ionization mass spectrometry in the analysis of chemical food contaminants in food", Trac Trends in Analytical Chemistry, 30(2):165-180 (2011).

Boughton, B. et al., "Mass spectrometry imaging for plant biology: a review", Phytochemistry Reviews, 15(3):445-488 (2015).

Schafer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.

International Search Report and Written Opinion for International Application No. PCT/GB2016/052956, dated Jan. 26, 2017, 16 pages.

Hsu, et al., "Microscopy ambient ionization top-down mass spectrometry reveals developmental patterning", Proceedings of the National Academy of Sciences, vol. 110, No. 37, pp. 14855-14860, Aug. 22, 2013.

Na, N., et al., "Development of a Dielectric Barrier Discharge Ion Source for Ambient Mass Spectrometry", Journal of The American Society for Mass Spectrometry, Elsevier Science Inc, vol. 18, No. 10, pp. 1859-1862, Sep. 20, 2007.

Jackson, S. N. et al. "On-line laser desorption/ionization mass spectrometry of matrix-coated aerosols", Rapid Communications in Mass Spectrometry, vol. 18, pp. 2041-2045 (Year: 2004).

Dong, Y., et al., "Sample Preparation for Mass Spectrometry Imaging of Plant Tissues: A Review", Frontiers in Plant Science 7(60): 1-16 (2016).

Communication pursuant to Article 94(3) EPC, for application No. 16710788.7, dated Jun. 13, 2019, 9 pages.

Examination Report under Section 18(3), for application No. GB1714122.7, dated May 9, 2019, 6 pages.

Cho, YT., et al. "Differentiation of Virulence of Helicobacter Pyloriby Matrix-Assited Laser Desorption/Ionization Mass Spectrometry and Multivariate Analyses" Clinica Chimica Acta, Elsevier BV, 424:123-130, May 26, 2013.

Chen et al. "Desorption Electrospray Ionization Mass spectrometry for high-thoughput analysis of Pharamaceutical samples in the ambient environment" (Year: 2005).

Harry, K. H., et al. "Effect of protein coating of flocked swabs on the collection and release of clinically important bacteria", Indian Journal of Medical Microbiology, 32(3):301-303 (2014).

Blais, B. W., "Swab-Based Enzyme Immunoassay System for Detection of Meat Residues on Food Contact Surfaces as a Hygiene Monitoring Tool", Journal of Food Protection, 62(4):386-389 (1999).

Farhat, S. E., et al., "Efficacy of a Swab Transport System in Maintaining Viability of Neisseria gonorrhoeae and *Streptococcus pneumoniae*", Journal of Clinical Microbiology, 39(8):2958-2960 (2001).

Hachmoeller et al., "Element bioimaging of liver needle biopsy specimens from patients with Wilsons disease by laser ablation-inductively coupled plasma-mass spectrometry", Journal of Trace Elements in Medicine and Biology, 35:97-102, Feb. 10, 2016.

Guenther et al., ""Spatially Resolved Metabolic Phenotyping of Breast Cancer by Desorption Electrospray Ionization Mass Spectrometry"", Cancer Research, 75:1828-1837, Feb. 17, 2015.

Santagata, S., et al., "Intraoperative mass spectrometry mapping of an onco-metabolite to guide brain tumor surgery", Proceedings of the National Academy of Sciences (PNAS), 111(30):11121-11126, Jun. 30, 2014.

Chipuk, J. E., et al., "Transmission Mode Desorption Electrospray Ionization", Journal of the American Society for Mass Spectrometry, 19(11):1612-1620, Nov. 1, 2008.

Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.

Sankaranarayanan, G. et al., "Common Uses and Cited Complications of Energy in Surgery", Surg Endosc., 27:3056-3072, (2013).

Rau, H.G., et al., "The use of water-jet dissection in open and laparoscopic liver resection", HPB, 10: 275280, (2008).

Chen, H., et al., "What Can We Learn from Ambient Ionization Techniques", Journal of the American Society for Mass Spectrometry, 20:1947-1963, (2009).

Office Action for CN Patent Application No. 201680025801.0 dated Apr. 7, 2020.

CNOA for Application No. 201910350273.1 dated May 8, 2021, 15 pages.

* cited by examiner

CAPACITIVELY COUPLED REIMS TECHNIQUE AND OPTICALLY TRANSPARENT COUNTER ELECTRODE

CROSS-REFERENCE TO RELATED APPLICATIONS

This application is a continuation application of U.S. patent application Ser. No. 15/764,791, filed Mar. 29, 2018, which is the National Stage of International Application No. PCT/GB2016/052956, filed Sep. 22, 2016, which claims priority from and the benefit of United Kingdom Patent Application No. 1517195.2, filed Sep. 29, 2015. The entire contents of these applications are incorporated herein by reference.

FIELD OF THE INVENTION

The present invention relates generally to mass spectrometers and in particular to the analysis of material by rapid evaporation ionisation mass spectrometry ("REIMS").

BACKGROUND

Rapid evaporation ionisation mass spectrometry ("REIMS") is a relatively new technique that is useful for the analysis of many different samples including the identification of tissue such as food. For example, it is known to use rapid evaporation ionisation mass spectrometry to determine the animal of origin of a food sample and also the pathological state of a tissue sample. It is also known to use rapid evaporation ionisation mass spectrometry to identify microbes, yeast and fungi.

The known approach for analysing bacterial colonies by rapid evaporation ionisation mass spectrometry involves using bipolar electrosurgical forceps and an electrosurgical RF generator. A bacterial colony is scraped from the surface of an agar layer using the bipolar electrosurgical forceps and a short burst of RF voltage from the electrosurgical RF generator is applied between the bipolar electrosurgical forceps. For example, it is known to apply 60 W of power in a bipolar mode at a frequency of 470 kHz sinusoid. The RF voltage which is applied to the electrosurgical forceps has the result of rapidly heating the particular portion of the bacterial colony which is being analysed due to its nonzero impedance. The rapid heating of the microbial mass results in an aerosol being generated. The aerosol is transferred directly into a mass spectrometer and the aerosol sample may then be analysed by the mass spectrometer. It is known for the control system of the mass spectrometer to utilise multivariate statistical analysis in order to help distinguish and identify different samples.

Rapid evaporation ionisation mass spectrometry is, therefore, a form of mass spectrometry that uses high frequency energy to ablate or vaporise a sample wherein the resulting vapour or aerosol is then subjected to mass spectrometry.

Conventional rapid evaporation ionisation mass spectrometry analysis involves ensuring that the sample is in direct electrical (and physical) contact with a RF voltage supply. This approach works well for tissue identification either ex vivo or in vivo. However, such an approach is problematic if it is desired to process a sample which is housed in a container. In particular, the known approach is problematic if it is desired to process a bacterial culture grown on agar in a petri dish.

It is also problematic to attempt to use the known arrangement for the analysis of tissue sections mounted on a glass slide when it is desired to analyse the tissue sections optically and also to subject the tissue sections to REIMS microprobe imaging.

For completeness, it should be mentioned that other forms of analysis are known such as Matrix Assisted Laser Desorption Ionisation ("MALDI") analysis. However, such approaches are quite different to REIMS and involve looking at the protein/peptide fingerprint of a sample. This is a relatively slow process that requires significant sample preparation and hence such a process is problematic.

N. Strittmatter, M. Rebec, E. Jones, O. Golf, A. Abdolrasouli, J. Balog, V. Behrends, K. Veselkov, Z. Takats "Characterization and Identification of Clinically Relevant Microorganisms Using Rapid Evaporative Ionization Mass Spectrometry" Anal. Chem. 2014, 86, 6555-6562 discloses a known arrangement wherein two hand-held electrodes in the form of a forceps are used to scrape microbial biomass off from an agar surface. The two electrodes are then squeezed together so as to pinch the biomass between the tips of the forceps. RF power is then applied to the biomass and an aerosol containing analytes is passed to a mass spectrometer for analysis. Accordingly, this reference discloses effectively resistive heating of a sample wherein current flows from one electrode through the sample to the other electrode. Power is dissipated in the sample via resistive heating.

It is desired to provide an improved method of analysing a sample and in particular an improved method of analysing a sample which may comprise a biological sample which has been grown on a culture medium and which is provided in, for example, a petri dish.

SUMMARY

According to an aspect there is provided a method of analysis comprising:

providing a sample on an insulating substrate;

contacting the insulating substrate with a first electrode and contacting the sample with a second electrode; and applying an AC or RF voltage to the first and second electrodes in order to generate an aerosol from the sample.

The known arrangement disclosed in N. Strittmatter, M. Rebec, E. Jones, O. Golf, A. Abdolrasouli, J. Balog, V. Behrends, K. Veselkov, Z. Takats "Characterization and Identification of Clinically Relevant Microorganisms Using Rapid Evaporative Ionization Mass Spectrometry" Anal. Chem. 2014, 86, 6555-6562 does not disclose contacting an insulating substrate such as a petri dish with a first electrode and contacting the sample with a second electrode.

In particular, according to various embodiments the sample may be cultured on or within a solid or liquid culture or growth medium wherein both the sample and culture or growth medium are provided on the insulating substrate which may comprise a container, petri dish, a vial or a microtitre plate. A bottom surface of the container, petri dish, vial or microtitre plate may be brought into contact with the first electrode which may be positioned below the container, petri dish, vial or microtitre plate. The second electrode may be brought into contact with the sample and/or culture or growth medium. It will be appreciated that the insulating substrate is located between the first and second electrodes when the AC or RF voltage is applied to the first and second electrodes. As a result, electrical energy is predominantly capacitively coupled into the sample. The known arrangement referred to above does not disclose capacitively coupling electrical energy into a sample by bringing a first electrode into contact with the bottom surface of a container, petri dish, vial or microtitre plate containing the sample whilst a second electrode is brought into contact with the sample such that the housing or body of the insulating substrate (i.e. insulating container, petri dish, vial or microtitre plate) is intermediate or between the first and second electrodes when the AC or RF voltage is applied to the first and second electrodes.

The method may further comprise locating the insulating substrate upon the first electrode, wherein the insulating substrate (e.g. container, petri dish, vial or microtitre plate) is optically transparent or optically translucent and wherein the first electrode is also substantially optically transparent or translucent. The method may further comprise passing light or photons through the first (transparent) electrode and the (transparent) insulating substrate in order to illuminate, image or analyse the sample. The known arrangement does not disclose providing an optically transparent electrode or passing light through an optically transparent electrode in order to illuminate a sample.

The sample may comprise a biological, bacterial, fungal or yeast sample or a cell line which has been cultured on to or within a culture or growth medium. The culture or growth medium may comprise a solid or liquid culture or growth medium.

For example, the culture or growth medium may comprise an agar-based medium, a carbohydrate matrix or another solid growth medium.

Alternatively, the culture or growth medium may comprise a liquid medium, a cell growth medium such as but not limited to DME (Dulbecco's Modified Eagle's medium), a modified DME medium (e.g. glucose or glutamine free), RPMI (Roswell Park Memorial Institute medium), MEM (Minimum Essential Medium), IMDM (Iscove's Modified Dulbecco's Medium) or another liquid growth medium.

The sample may be spun down using a centrifuge to form a pellet and the supernate may be discarded or used for subsequent analysis.

The sample or pellet may be smeared onto a glass slide or other insulating surface, or may be anlaysed in situ.

The sample may be provided on or in a container, a petri dish, a vial or a microtitre or microwell plate. The microtitre or microwell plate may, for example, comprise 6, 24, 96, 384 or 1536 wells.

The step of providing the sample on the insulating substrate may further comprise providing the sample and optional culture or growth medium on a first surface of the insulating substrate.

The step of contacting the insulating substrate with the first electrode may further comprise contacting the insulating substrate with the first electrode on a second surface of the insulating substrate which is opposed to the first surface.

The step of contacting the insulating substrate with the first electrode may be such that the first electrode does not contact the sample.

The step of contacting the insulating substrate with the first electrode may be such that the first electrode does not contact any culture or growth medium.

The step of applying an AC or RF voltage to the first and second electrodes may be such that electrical energy is predominantly capacitively coupled into the sample.

The transfer of electrical energy into the sample may cause the aerosol to be generated.

The method may further comprise ionising at least some of the aerosol so as to generate analyte ions.

The method may comprise directing at least some of the aerosol into a vacuum chamber of a mass spectrometer.

The method may further comprise ionising at least some of the aerosol within a or the vacuum chamber of the mass spectrometer so as to generate a plurality of analyte ions.

The method may further comprise mass analysing the analyte ions.

The method may further comprise obtaining mass spectral data corresponding to one or more locations on or in the sample.

The method may further comprise spectroscopically imaging or analysing the sample.

The step of spectroscopically imaging or analysing the sample may further comprise spectroscopically imaging or analysing the sample at substantially the same time as obtaining mass spectral data corresponding to one or more locations on or in the sample.

The step of spectroscopically imaging or analysing the sample may comprise subjecting the sample to Raman spectroscopy and/or to infra-red ("IR") spectroscopy.

The step of subjecting the sample to Raman spectroscopy and/or to infra-red ("IR") spectroscopy may further comprise: (i) determining one or more physico-chemical properties of the sample; (ii) determining one or more chemical properties of the sample; (iii) determining one or more absorption properties of the sample; or (iv) determining one or more vibrational and/or rotational modes or states of the sample.

The method may further comprise using the obtained mass spectral data to identify one or more biological substances, one or more bacterial strains, one or more fungal strains, one or more yeast strains or one or more cell lines located at one or more locations on or in the sample.

The method may further comprise optically or visually identifying one or more regions of interest on or in the sample.

The step of optically or visually identifying one or more regions of interest on or in the sample may comprise using a video camera or a digital camera to obtain one or more images of the sample.

The method may further comprise processing the one or more images of the sample in order to determine one or more regions of interest on or in the sample.

The first and second electrodes may comprise a rapid evaporation ionization mass spectrometry ("REIMS") device.

The rapid evaporation ionization mass spectrometry ("REIMS") device may comprise a monopolar device.

The step of applying the AC or RF voltage to the first and second electrodes may further comprise applying one or more pulses of the AC or RF voltage to the first and second electrodes.

The step of applying the AC or RF voltage to the first and second electrodes may cause heat to be dissipated into the sample.

The sample may comprise a biological, bacterial, fungal or yeast sample or a cell line which has been cultured on to or within a culture or growth medium. The culture or growth medium may comprise a solid or liquid culture or growth medium.

For example, the culture or growth medium may comprise an agar-based medium, a carbohydrate matrix or another solid growth medium.

Alternatively, the culture or growth medium may comprise a liquid medium, a cell growth medium such as but not limited to DME (Dulbecco's Modified Eagle's medium), a modified DME medium (e.g. glucose or glutamine free), RPMI (Roswell Park Memorial Institute medium), MEM (Minimum Essential Medium), IMDM (Iscove's Modified Dulbecco's Medium) or another liquid growth medium.

The sample may be spun down using a centrifuge to form a pellet and the supernate may be discarded or used for subsequent analysis.

The sample or pellet may be smeared onto a glass slide or other insulating surface, or may be anlaysed in situ.

The method may further comprise determining a spatial distribution of one or more excreted substances emanating from one or more biological substances, one or more bacterial colonies, one or more fungal colonies, one or more yeast colonies or one or more cell lines which have been cultured on or within the culture or growth medium.

The one or more excreted substances may be selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; (xx) one or more ribosomal peptides; and (xxi) one or more drugs or toxins.

The method may further comprise providing the sample in a container, petri dish, a vial or a microtitre or microwell plate. The microtitre or microwell plate may, for example, comprise 6, 24, 96, 384 or 1536 wells.

The first electrode may comprise a mesh electrode.

The first electrode may comprise a substrate which is substantially optically transparent or optically translucent.

The substrate may comprise glass, plastic, polycarbonate, poly(methyl methacrylate), Plexiglas® or quartz.

The substrate may further comprise a conductive layer or a conductive coating.

The conductive layer or the conductive coating may be substantially optically transparent or optically translucent.

The conductive layer or the conductive coating is selected from the group consisting of: (i) a conductive oxide layer or coating; (ii) indium-tin oxide; (iii) aluminium-doped zinc oxide ("AZO"); (iv) indium-doped cadmium oxide; (v) aluminium-doped zinc oxide ("AZO"); (vi) gallium-doped zinc oxide ("GZO"); (vii) indium-doped zinc oxide ("IZO"); (viii) a metallic layer; (ix) a carbon nanotube conductive coating; (x) a graphene film; (xi) one or more silver nanowires covered with graphene; (xii) a polymeric layer; (xiii) polyaniline; or (xiv) a poly(3,4-ethylenedioxythiophene): poly(styrenesulfonate) ("PEDOT:PSS") composite.

According to an aspect there is provided a method of rapid evaporation ionization mass spectrometry ("REIMS") comprising a method as described above.

According to an aspect there is provided a method of mass spectrometry comprising a method as described above.

According to an aspect there is provided analysis apparatus comprising:

a first electrode for contacting an insulating substrate upon which a sample is located in use;

a second electrode for contacting the sample; and a device for applying an AC or RF voltage to the first and second electrodes in order to generate an aerosol from the sample.

The known arrangement disclosed in N. Strittmatter, M. Rebec, E. Jones, O. Golf, A. Abdolrasouli, J. Balog, V. Behrends, K. Veselkov, Z. Takats "Characterization and Identification of Clinically Relevant Microorganisms Using Rapid Evaporative Ionization Mass Spectrometry" Anal. Chem. 2014, 86, 6555-6562 does not disclose contacting an insulating substrate such as a petri dish with a first electrode and contacting the sample with a second electrode.

In particular, according to various embodiments the sample may be cultured on or within a culture medium wherein both the sample and culture medium are provided on the insulating substrate which may comprise a container, petri dish, a vial or microtitre or microwell plate. The microtitre or microwell plate may, for example, comprise 6, 24, 96, 384 or 1536 wells. A bottom surface of the container, petri dish, vial or microtitre plate may be brought into contact with the first electrode which may be positioned below the container, petri dish, vial or microtitre plate. The second electrode may be brought into contact with the sample and/or culture medium. It will be appreciated that the insulating substrate is located in between the first and second electrodes when the AC or RF voltage is applied to the first and second electrodes. As a result, electrical energy is predominantly capacitively coupled into the sample. The known arrangement referred to above does not disclose capacitively coupling electrical energy into a sample by bringing a first electrode into contact with the bottom surface of a container, petri dish, vial or petri dish containing the sample whilst a second electrode is brought into contact with the sample such that the housing or body of the insulating substrate (i.e. insulating container, petri dish, vial or microtitre plate) is intermediate or between the first and second electrodes when the AC or RF voltage is applied to the first and second electrodes.

According to an embodiment the insulating substrate may be located, in use, upon the first electrode and the insulating substrate (e.g. container, petri dish, vial or microtitre plate) may be optically transparent or optically translucent and the first electrode may also be substantially optically transparent or translucent. The apparatus may further comprise a device arranged and adapted to pass light or photons through the first (transparent) electrode and the (transparent) insulating substrate in order to illuminate, image or analyse the sample. The known arrangement does not disclose providing an optically transparent electrode or passing light through an optically transparent electrode in order to illuminate a sample.

The sample may comprise a biological, bacterial, fungal or yeast sample or a cell line which has been cultured on to or within a culture or growth medium. The culture or growth medium may comprise a solid or liquid culture or growth medium.

For example, the culture or growth medium may comprise an agar-based medium, a carbohydrate matrix or another solid growth medium.

Alternatively, the culture or growth medium may comprise a liquid medium, a cell growth medium such as but not limited to DME (Dulbecco's Modified Eagle's medium), a modified DME medium (e.g. glucose or glutamine free), RPMI (Roswell Park Memorial Institute medium), MEM (Minimum Essential Medium), IMDM (Iscove's Modified Dulbecco's Medium) or another liquid growth medium.

The sample may be spun down using a centrifuge to form a pellet and the supernate may be discarded or used for subsequent analysis.

The sample or pellet may be smeared onto a glass slide or other insulating surface, or may be anlaysed in situ.

The sample may be provided on or in a container, petri dish, vial or a microtitre or microwell plate. The microtitre or microwell plate may, for example, comprise 6, 24, 96, 384 or 1536 wells.

The sample and optionally a culture or growth medium may be provided on a first surface of the insulating substrate.

The first electrode may be arranged to contact a second surface of the insulating substrate which is opposed to the first surface.

According to an embodiment the first electrode does not contact the sample in use.

According to an embodiment the first electrode does not contact any culture or growth medium in use.

The device for applying an AC or RF voltage to the first and second electrodes may be arranged and adapted to predominantly capacitively couple electrical energy into the sample.

The transfer of electrical energy into the sample may cause the aerosol to be generated.

The apparatus may further comprise an ion source for ionising at least some of the aerosol so as to generate analyte ions.

The apparatus may further comprise a device for directing at least some of the aerosol into a vacuum chamber of a mass spectrometer.

The apparatus may further comprise an ion source located within a or the vacuum chamber of the mass spectrometer for ionising at least some the aerosol so as to generate a plurality of analyte ions.

The apparatus may further comprise a mass analyser for mass analysing the analyte ions.

The mass analyser may be further arranged and adapted to obtain mass spectral data corresponding to one or more locations on or in the sample.

The apparatus may further comprise a spectroscopic imaging or analysing device for spectroscopically imaging or analysing the sample.

The spectroscopic imaging or analysing device may be arranged and adapted to spectroscopically image or analyse the sample at substantially the same time as the mass analyser obtains mass spectral data corresponding to one or more locations on or in the sample.

The spectroscopic imaging or analysing device may comprise a Raman spectroscope and/or an infra-red ("IR") spectroscope.

The Raman spectroscope and/or the infra-red ("IR") spectroscope may be arranged and adapted: (i) to determine one or more physico-chemical properties of the sample; (ii) to determine one or more chemical properties of the sample; (iii) to determine one or more absorption properties of the sample; or (iv) to determine one or more vibrational and/or rotational modes or states of the sample.

The apparatus may further comprise a control system arranged and adapted to use the obtained mass spectral data to identify one or more biological substances, one or more bacterial strains, one or more fungal strains, one or more yeast strains or one or more cell lines located at one or more locations on or in the sample.

The apparatus may further comprise a device for optically or visually identifying one or more regions of interest on or in the sample.

The apparatus may further comprise a video camera or a digital camera for obtaining one or more images of the sample.

The apparatus may further comprise a processor for processing the one or more images of the sample in order to determine one or more regions of interest on or in the sample.

The first and second electrodes may comprise a rapid evaporation ionization mass spectrometry ("REIMS") device.

The rapid evaporation ionization mass spectrometry ("REIMS") device may comprise a monopolar device.

The AC or RF voltage device may be arranged and adapted to apply one or more pulses of the AC or RF voltage to the first and second electrodes.

The AC or RF voltage device may be arranged and adapted to apply the AC or RF voltage to the first and second electrodes in order to cause heat to be dissipated into the sample.

The sample may comprise a biological, bacterial, fungal or yeast sample or a cell line which has been cultured on to or within a solid or liquid culture or growth medium.

The culture or growth medium may comprise an agar-based medium, a carbohydrate matrix or another solid growth medium.

The apparatus may further comprise a device for determining a spatial distribution of one or more excreted substances emanating from one or more biological substances, one or more bacterial colonies, one or more fungal, one or more yeast colonies or one or more cell lines which have been cultured on or within the culture or growth medium.

The one or more excreted substances may be selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; (xx) one or more ribosomal peptides; and (xxi) one or more drugs or toxins.

The sample may be provided in a container, petri dish, vial or a microtitre or microwell plate. The microtitre or microwell plate may, for example, comprise 6, 24, 96, 384 or 1536 wells.

The first electrode may comprise a mesh electrode.

The first electrode may comprise a substrate which is substantially optically transparent or optically translucent.

The substrate may comprise glass, plastic, polycarbonate, poly(methyl methacrylate), Plexiglas® or quartz.

The substrate may further comprise a conductive layer or a conductive coating.

The conductive layer or the conductive coating may be substantially optically transparent or optically translucent.

The conductive layer or the conductive coating may be selected from the group consisting of: (i) a conductive oxide layer or coating; (ii) indium-tin oxide; (iii) aluminium-doped zinc oxide ("AZO"); (iv) indium-doped cadmium oxide; (v) aluminium-doped zinc oxide ("AZO"); (vi) gallium-doped zinc oxide ("GZO"); (vii) indium-doped zinc oxide ("IZO"); (viii) a metallic layer; (ix) a carbon nanotube conductive coating; (x) a graphene film; (xi) one or more silver nanowires covered with graphene; (xii) a polymeric layer; (xiii)

polyaniline; or (xiv) a poly(3,4-ethylenedioxythiophene):poly(styrenesulfonate) ("PEDOT:PSS") composite.

According to an aspect there is provided a rapid evaporation ionization mass spectrometry ("REIMS") device comprising apparatus as described above.

According to an aspect there is provided a mass spectrometer comprising apparatus as described above.

According to an aspect there is provided a method of analysis comprising:

locating a sample on a first electrode;

passing light or photons through the first electrode in order to illuminate, image or analyse the sample;

contacting the sample with a second electrode; and applying an AC or RF voltage to the first and second electrodes in order to generate an aerosol from the sample.

The arrangement disclosed in N. Strittmatter, M. Rebec, E. Jones, O. Golf, A. Abdolrasouli, J. Balog, V. Behrends, K. Veselkov, Z. Takats "Characterization and Identification of Clinically Relevant Microorganisms Using Rapid Evaporative Ionization Mass Spectrometry" Anal. Chem. 2014, 86, 6555-6562 does not disclose passing light or photons through an electrode in order to illuminate, image or analyse a sample.

According to various embodiments a transparent counter electrode may be used in conjunction with rapid evaporation ionisation mass spectrometry in order to facilitate backlighting of a sample.

The transparent counter electrode also facilitates simultaneous spectroscopic imaging of the sample. Various embodiments are contemplated wherein a sample may be subjected to simultaneous REIMS and Raman spectroscopy or to simultaneous REIMS and infra-red ("IR") spectroscopy.

Various embodiments relate to the field of microorganism identification including the identification of bacteria, yeast, fungi or cell lines using rapid evaporation ionisation mass spectrometry. Other applications are contemplated which relate to rapid evaporation ionisation mass spectrometry tissue imaging.

According to other embodiments automated rapid evaporation ionisation mass spectrometry analysis of bacteria, yeast, fungal colonies or cell lines grown on agar or in a liquid growth medium may be performed. The colonies grown on agar or other culture media may be contained in a standard petri dish. Of particular interest is the fact that the colonies can be analysed directly from the petri dish (or other sample plate) without requiring any substantive intervention from a user or operator and without requiring any prior sample preparation.

According to an embodiment a spatial distribution of one or more excreted substances emanating from one or more biological substances, one or more bacterial colonies, one or more fungal colonies, one or more yeast colonies or one or more cell lines which have been cultured on or within a culture or growth medium may be determined. The one or more excreted substances may be selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; (xx) one or more ribosomal peptides; and (xxi) one or more drugs or toxins. It is known to use genetic engineering or modification of microbes and bacteria to force the production of novel compounds. This technique may be used to monitor the production of the compound and may also be used to screen the micro-organisms for unwanted mutations.

It will be apparent, therefore, that the various embodiments have significant benefits compared with known method of REIMS analysis.

The method may further comprise ionising at least some of the aerosol so as to generate analyte ions.

The method may further comprise directing at least some of the aerosol into a vacuum chamber of a mass spectrometer.

The method may further comprise ionising at least some the aerosol within a or the vacuum chamber of the mass spectrometer so as to generate a plurality of analyte ions.

The method may further comprise mass analysing the analyte ions.

The method may further comprise obtaining mass spectral data corresponding to one or more locations on or in the sample.

The step of passing light or photons through the first electrode may further comprise spectroscopically imaging or analysing the sample.

The step of spectroscopically imaging or analysing the sample may further comprise spectroscopically imaging or analysing the sample at substantially the same time as obtaining mass spectral data corresponding to one or more locations on or in the sample.

The step of spectroscopically imaging or analysing the sample may comprise subjecting the sample to Raman spectroscopy and/or to infra-red ("IR") spectroscopy.

The step of subjecting the sample to Raman spectroscopy and/or to infra-red ("IR") spectroscopy may further comprise: (i) determining one or more physico-chemical properties of the sample; (ii) determining one or more chemical properties of the sample; (iii) determining one or more absorption properties of the sample; or (iv) determining one or more vibrational and/or rotational modes or states of the sample.

The light or the photons may either: (i) be in the visible spectrum or have a wavelength in the range 390-700 nm; (ii) be in the near infra-red or have a wavelength in the range 700-1400 nm; or (iii) be in the near ultra-violet or have a wavelength in the range 300-390 nm.

The method may further comprise using the obtained mass spectral data to identify one or more biological substances, one or more bacterial strains, one or more fungal strains, one or more yeast strains or one or more cell lines located at one or more locations on or in the sample.

The method may further comprise optically or visually identifying one or more regions of interest on or in the sample.

The step of optically or visually identifying one or more regions of interest on or in the sample may comprise using a video camera or a digital camera to obtain one or more images of the sample.

The method may further comprise processing the one or more images of the sample in order to determine one or more regions of interest on or in the sample.

The first and second electrodes may comprise a rapid evaporation ionization mass spectrometry ("REIMS") device.

The rapid evaporation ionization mass spectrometry ("REIMS") device may comprise a monopolar device.

The step of applying the AC or RF voltage to the first and second electrodes may further comprise applying one or more pulses of the AC or RF voltage to the first and second electrodes.

The step of applying the AC or RF voltage to the first and second electrodes may cause heat to be dissipated into the sample.

The sample may comprise a biological, bacterial, fungal or yeast sample or a cell line which has been cultured on to or within a solid or liquid culture or growth medium.

The culture or growth medium may comprise an agar-based medium, a carbohydrate matrix or another solid growth medium.

Alternatively, the culture or growth medium may comprise a liquid medium, a cell growth medium such as but not limited to DME (Dulbecco's Modified Eagle's medium), a modified DME medium (e.g. glucose or glutamine free), RPMI (Roswell Park Memorial Institute medium), MEM (Minimum Essential Medium), IMDM (Iscove's Modified Dulbecco's Medium) or another liquid growth medium.

The sample may be spun down using a centrifuge to form a pellet and the supernate may be discarded or used for subsequent analysis.

The sample or pellet may be smeared onto a glass slide or other insulating surface, or may be anlaysed in situ.

The method may further comprise determining a spatial distribution of one or more excreted substances emanating from one or more biological substances, one or more bacterial colonies, one or more fungal colonies or one or more yeast colonies which have been cultured on to or within the culture or growth medium.

The one or more excreted substances may be selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; (xx) one or more ribosomal peptides; and (xxi) one or more drugs or toxins.

The method may further comprise providing the sample in a container, petri dish or a microtitre or microwell plate. The microtitre or microwell plate may, for example, comprise 6, 24, 96, 384 or 1536 wells.

The first electrode may comprise a mesh electrode.

The first electrode may comprise a substrate which is substantially optically transparent or optically translucent.

The substrate may comprise glass, plastic, polycarbonate, poly(methyl methacrylate), Plexiglas® or quartz.

The substrate may further comprise a conductive layer or a conductive coating.

The conductive layer or the conductive coating may be substantially optically transparent or optically translucent.

The conductive layer or the conductive coating may be selected from the group consisting of: (i) a conductive oxide layer or coating; (ii) indium-tin oxide; (iii) aluminium-doped zinc oxide ("AZO"); (iv) indium-doped cadmium oxide; (v) aluminium-doped zinc oxide ("AZO"); (vi) gallium-doped zinc oxide ("GZO"); (vii) indium-doped zinc oxide ("IZO"); (viii) a metallic layer; (ix) a carbon nanotube conductive coating; (x) a graphene film; (xi) one or more silver nanowires covered with graphene; (xii) a polymeric layer; (xiii) polyaniline; or (xiv) a poly(3,4-ethylenedioxythiophene): poly(styrenesulfonate) ("PEDOT:PSS") composite.

According to an aspect there is provided a method of rapid evaporation ionization mass spectrometry ("REIMS") comprising a method as described above.

According to an aspect there is provided a method of mass spectrometry comprising a method as described above.

According to an aspect there is provided analysis apparatus comprising:

a first electrode;

a first device for passing light or photons through the first electrode in order to illuminate, image or analyse, in use, a sample located on the first electrode;

a second electrode for contacting the sample; and a second device for applying an AC or RF voltage to the first and second electrodes in order to generate an aerosol from the sample.

The arrangement disclosed in N. Strittmatter, M. Rebec, E. Jones, O. Golf, A. Abdolrasouli, J. Balog, V. Behrends, K. Veselkov, Z. Takats "Characterization and Identification of Clinically Relevant Microorganisms Using Rapid Evaporative Ionization Mass Spectrometry" Anal. Chem. 2014, 86, 6555-6562 does not disclose passing light or photons through an electrode in order to illuminate, image or analyse a sample.

The apparatus may further comprise an ion source for ionising at least some of the aerosol so as to generate analyte ions.

The apparatus may further comprise a device for directing at least some of the aerosol into a vacuum chamber of a mass spectrometer.

The apparatus may further comprise an ion source located within a or the vacuum chamber of the mass spectrometer for ionising at least some the aerosol so as to generate a plurality of analyte ions.

The apparatus may further comprise a mass analyser for mass analysing the analyte ions.

The mass analyser may be arranged and adapted to obtain mass spectral data corresponding to one or more locations on or in the sample.

The first device may comprise a spectroscopic imaging or analysing device for spectroscopically imaging or analysing the sample.

The spectroscopic imaging or analysing device may be arranged and adapted to spectroscopically image or analyse the sample at substantially the same time as the mass analyser obtains mass spectral data corresponding to one or more locations on or in the sample.

The spectroscopic imaging or analysing device may comprise a Raman spectroscope and/or an infra-red ("IR") spectroscope.

The Raman spectroscope and/or the infra-red ("IR") spectroscope may be arranged and adapted: (i) to determine one or more physico-chemical properties of the sample; (ii) to determine one or more chemical properties of the sample; (iii) to determine one or more absorption properties of the sample; or (iv) to determine one or more vibrational and/or rotational modes or states of the sample.

According to an embodiment the light or the photons may either: (i) be in the visible spectrum or have a wavelength in the range 390-700 nm; (ii) be in the near infra-red or have a wavelength in the range 700-1400 nm; or (iii) be in the near ultra-violet or have a wavelength in the range 300-390 nm.

The apparatus may further comprise a control system which is arranged and adapted to use the obtained mass spectral data to identify one or more biological substances, one or more bacterial strains, one or more fungal strains, one or more yeast strains or one or more cell lines located at one or more locations on or in the sample.

The apparatus may further comprise a control system which is arranged and adapted to optically or visually identify one or more regions of interest on or in the sample.

The apparatus may further comprise a video camera or a digital camera for obtaining one or more images of the sample.

The apparatus may further comprise a processor for processing the one or more images of the sample in order to determine one or more regions of interest on or in the sample.

The first and second electrodes may comprise a rapid evaporation ionization mass spectrometry ("REIMS") device.

The rapid evaporation ionization mass spectrometry ("REIMS") device may comprise a monopolar device.

The device for applying the AC or RF voltage to the first and second electrodes may be arranged and adapted to apply one or more pulses of the AC or RF voltage to the first and second electrodes.

The device for applying the AC or RF voltage to the first and second electrodes may be arranged and adapted to cause heat to be dissipated into the sample.

The sample may comprise a biological, bacterial, fungal or yeast sample or a cell line which has been cultured on to or within a solid or liquid culture or growth medium.

The culture or growth medium may comprise an agar-based medium, a carbohydrate matrix or another solid growth medium.

Alternatively, the culture or growth medium may comprise a liquid medium, a cell growth medium such as but not limited to DME (Dulbecco's Modified Eagle's medium), a modified DME medium (e.g. glucose or glutamine free), RPMI (Roswell Park Memorial Institute medium), MEM (Minimum Essential Medium), IMDM (Iscove's Modified Dulbecco's Medium) or another liquid growth medium.

The sample may be spun down using a centrifuge to form a pellet and the supernate may be discarded or used for subsequent analysis.

The sample or pellet may be smeared onto a glass slide or other insulating surface, or may be anlaysed in situ.

The apparatus may further comprise a device for determining a spatial distribution of one or more excreted substances emanating from one or more biological substances, one or more bacterial colonies, one or more fungal colonies, one or more yeast colonies or one or more cell lines which have been cultured on or within the culture or growth medium.

The one or more excreted substances may be selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; (xx) one or more ribosomal peptides; and (xxi) one or more drugs or toxins.

The sample may be provided in a container, petri dish or a microtitre or microwell plate. The microtitre or microwell plate may, for example, comprise 6, 24, 96, 384 or 1536 wells.

The first electrode may comprise a mesh electrode.

The first electrode may comprise a substrate which is substantially optically transparent or optically translucent.

The substrate may comprise glass, plastic, polycarbonate, poly(methyl methacrylate), Plexiglas® or quartz.

The substrate may further comprise a conductive layer or a conductive coating.

The conductive layer or the conductive coating may be substantially optically transparent or optically translucent.

The conductive layer or the conductive coating may be selected from the group consisting of: (i) a conductive oxide layer or coating; (ii) indium-tin oxide; (iii) aluminium-doped zinc oxide ("AZO"); (iv) indium-doped cadmium oxide; (v) aluminium-doped zinc oxide ("AZO"); (vi) gallium-doped zinc oxide ("GZO"); (vii) indium-doped zinc oxide ("IZO"); (viii) a metallic layer; (ix) a carbon nanotube conductive coating; (x) a graphene film; (xi) one or more silver nanowires covered with graphene; (xii) a polymeric layer; (xiii) polyaniline; or (xiv) a poly(3,4-ethylenedioxythiophene): poly(styrenesulfonate) ("PEDOT:PSS") composite.

According to an aspect there is provided a rapid evaporation ionization mass spectrometry ("REIMS") device comprising apparatus as described above.

According to an aspect there is provided a mass spectrometer comprising apparatus as described above.

BRIEF DESCRIPTION OF THE DRAWINGS

Various embodiments will now be described, by way of example only, and with reference to the accompanying drawings in which.

DETAILED DESCRIPTION

Figure 1:
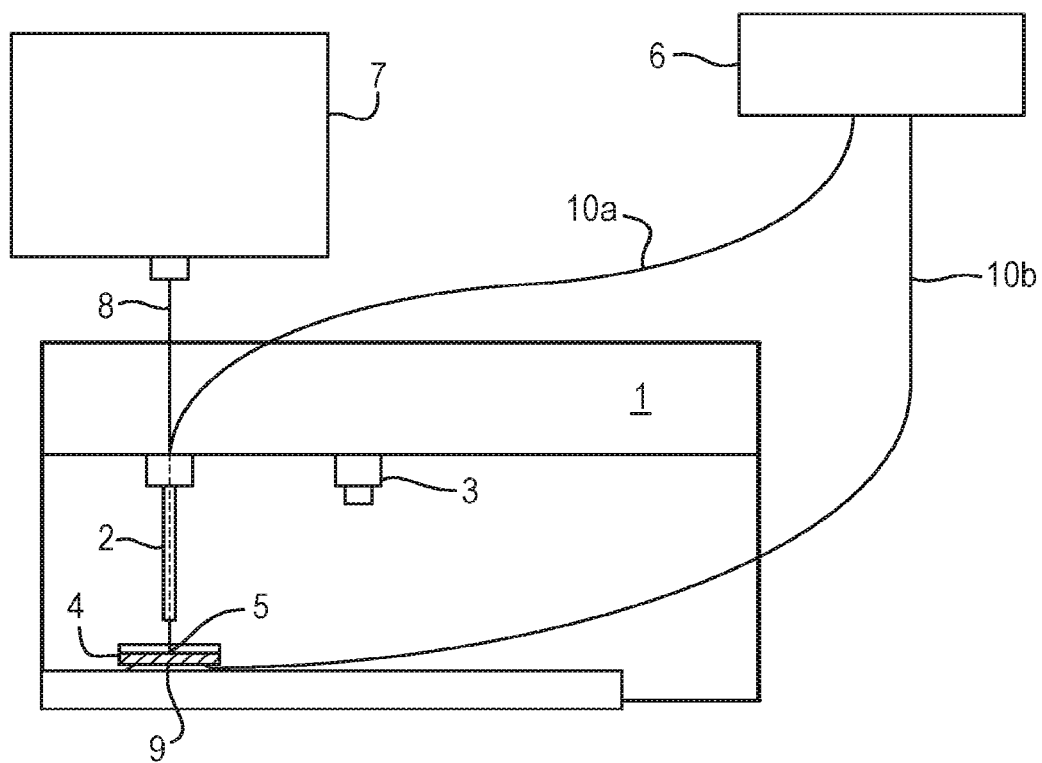
FIG. 1 shows a schematic of an automated microbial sampling system according to an embodiment and shows a REIMS sampling probe located above a sample which is provided in a petri dish.

Various embodiments will now be described in the context of seeking to aid high throughput microbe identification. However, it should be understood that the various embodiments described herewith are merely illustrative and that the present invention is not intended to be limited to microbe identification.

According to an arrangement it is contemplated that a two-electrode (bipolar) sampling probe might be used to analyse a sample. However, using a two-electrode sampling probe is potentially problematic since a two-electrode sampling probe has an increased physical size at the point of contact with the sample. It is also necessary to avoid electrical breakdown between the two electrodes forming the probe and to take steps to avoid potential problems due to cross contamination effects.

According to other arrangements a single analysis probe (e.g. monopolar electrode) may be used to vaporize or ablate a colony and an additional probe (or counter electrode) may be used to make direct electrical and physical contact with the bulk media or agar. Although this approach has been demonstrated to work (to some extent) it suffers from the problem that it requires an additional probe (or counter electrode) to be provided which needs to contact the bulk media or agar. Furthermore, this approach suffers from the problem of having a restricted available analysis area as the heating effect scales quadratically with the current density. It has been recognised that ideally the sampling probe area should be relatively small whereas the additional probe (or counter electrode) should be relatively large so as to avoid heating at the additional probe (or counter electrode).

Further embodiments which are of particular interest will now be described in more detail below. These embodiments are of particular interest since they eliminate any need for an additional probe (or counter electrode) to be placed in direct physical contact with the bulk material e.g. agar or other culture or growth medium thereby avoiding the problem of cross contamination.

The various embodiments which will now be described in more detail below are of particular interest since they enable a precise region of a colony to be analysed without suffering from heating effects at the counter electrode. Furthermore, these embodiments do not suffer from potential cross contamination effects. A yet further beneficial effect is that the various embodiments described below significantly improve the ability to illuminate a sample in order to identify one or more regions of interest to be analysed.

According to various embodiments a sample to be analysed (such as a microbe colony) may be located or provided on a culture or growth medium such as agar. The sample and the culture or growth medium on which it may have been grown may be located or provided in a petri dish, vial or other container such as a microtitre plate or microwell plate. The microtitre or microwell plate may, for example, comprise 6, 24, 96, 384 or 1536 wells. As will become more apparent below, the sample which has been grown on the culture or growth medium in the petri dish can be analysed in situ in the petri dish. This is of particular interest since conventional approaches require a sample portion to be scraped off the surface of the agar or other culture or growth medium and to be analysed whilst being held by a pair of electrosurgical forceps.

The petri dish or other container in which the sample and culture or growth medium may be provided may be made from glass or plastic. As a result, the petri dish or other container may be essentially electrically non-conductive or may comprise an electrical insulator.

According to various embodiments a first or counter electrode may be located underneath (or otherwise in close proximity to) the lower or bottom surface of a petri dish or other container so that the petri dish or other container (which is an insulator) sits or otherwise rests upon the first or counter electrode.

According to various embodiments the first or counter electrode may be arranged to have a similar surface area to that of the petri dish or other container which contains the sample to be analysed.

According to various embodiments a rapid evaporation ionisation mass spectrometry ("REIMS") sampling system may be provided which comprises a first (counter) electrode which is placed below or underneath an insulating petri dish (or other container) and a second (sample probe) electrode which is brought into direct physical contact with the sample to be analysed in the petri dish (or other container).

According to an embodiment a REIMS sample probe electrode may be brought into contact (from above) with a microbe colony to be analysed and identified whilst a first or counter electrode is located below the petri dish or other container containing the sample to be analysed.

An AC or RF voltage may be applied between the REIMS sample probe electrode (which is direct contact with the sample to be analysed) and the REIMS counter electrode (which is in contact with the rear or lower surface of the petri dish or other container containing the sample and optional culture or growth medium). It will be apparent, therefore, that the REIMS counter electrode is not brought into direct physical with the sample to be analysed. This enables the REIMS counter electrode to be reused without suffering from any cross contamination problems.

According to various embodiments the application of the AC or RF voltage to the first (counter) electrode and the second (sample probe) electrode causes a current to flow but it will be apparent that since the REIMS counter electrode is in electrical or direct physical contact with an insulator (i.e. the bottom of a petri dish) then the petri dish and the contents of the petri dish (i.e. the culture or growth medium) effectively form a dielectric of a capacitor. Therefore, as a result, electrical energy is predominantly capacitively coupled into the sample.

It will be understood that this approach is therefore quite different from the known approach wherein bipolar electrosurgical forceps are used to remove a sample from a culture or growth medium and wherein both electrodes are brought into direct physical and electrical contact with the sample.

In contrast to the known approach, the first (counter) electrode does not make direct physical contact with the sample to be analysed and energy is capacitively coupled into the sample in order to rapidly heat and vaporise the sample thereby generating an aerosol to be analysed.

The frequency of the applied AC or RF voltage may be maximized so as to ensure that the electrical impedance of the bulk material is essentially minimised thereby resulting in maximum energy dissipation into the sample which is desired to be analysed. As a result, AC or RF energy is capacitively coupled into the microbe colony with the result that a portion of the microbe colony in the immediate vicinity of the REIMS probe electrode is vapourised so as to form an aerosol.

A particular embodiment will now be described in more detail with reference to FIG. 1. FIG. 1 shows an embodiment comprising a commercial robotic system 1 such as, for example, a Tecan EVO® robotic system together with a Picolo® colony identification system. The commercial robotic system 1 has been modified so as to include a REIMS sampling probe electrode 2 and a REIMS counter electrode 9. The REIMS sampling probe electrode 2 and the REIMS counter electrode 9 are connected to an electrosurgical RF generator 6 via a feed electrode 10a and a counter or return electrode 10b respectively.

Colonies grown on a culture or growth medium (such as agar) in a petri dish 4 or other container may be identified using a video camera system 3 which may, for example, be attached to a robotic arm of the robotic system 1. Images of any colonies which have grown on the culture or growth medium may then be processed by digital image processing software. According to an embodiment Picolo® digital imaging processing software may be used to process images of any colonies which have grown on the culture or growth medium.

The robotic arm of the robotic system 1 may be arranged to position the video camera system 3 above the petri dish 4 so that one or more digital pictures of the colony may be recorded. The digital image processing software may then analyse the picture(s) and identify the colonies. Colonies may be selected according to various predetermined criteria or may be manually selected from a video picture.

The REIMS sampling probe (or head) 2 may be moved directly above selected colonies and the position of the surface of a colony relative to e.g. the tip 5 of the REIMS sampling probe 2 may be determined using a built-in capacitive probe. According to various embodiments the tip 5 of the REIMS sampling probe 2 may be moved so that the tip 5 of the sampling probe 2 just contacts and makes physical contact with a selected colony. REIMS sampling may then be performed by briefly energizing the RF generator 6.

One pole of the RF generator 6 may be connected to the tip 5 of the REIMS sampling probe 2 via the feed electrode cable 10a and the other pole of the RF generator 6 may be connected to the counter electrode 9 (located in use underneath the petri dish 4 or other container) by the counter electrode cable 10b.

A RF voltage may be applied to a selected colony by, for example, applying a pulse of a RF voltage via the cables 10a,10b to the tip 5 of the REIMS sampling probe 2 and also to the REIMS counter electrode 9 located underneath the petri dish 4 or other container. As a result of capacitively coupling electrical energy into the sample, surgical fumes or an aerosol of sample material may be generated. The surgical fumes or aerosol of sample material may then be passed via a tube 8 or other conduit (which may be attached to the REIMS sampling probe 2) directly into the housing of a mass spectrometer 7. According to an embodiment the surgical fumes or aerosol may be ionised within a vacuum chamber of the mass spectrometer 7 by an ion source which may be located within the vacuum chamber of the mass spectrometer 7.

In order for the image recognition software to be able to identify a colony as effectively as possible further embodiments which will be discussed in more detail below enable the petri dish 4 or other container to be illuminated from below the petri dish 4 or other container. Illumination of sample in a petri dish 4 or other container from below is beneficial since this enables clear colony boundaries to be observed by, for example, the camera system 3. Furthermore, illuminating the petri dish 4 or other container from below removes or substantially removes reflections (which would otherwise be observed) and also reduces the complexity of the overall optical system including the video camera system 3.

According to various embodiments which are of particular interest and which will be described in more detail below, the counter electrode 9 may comprise a transparent substrate (e.g. glass or plastic) having a transparent conductive coating on e.g. an upper surface so as to form a transparent electrode on the transparent substrate.

Other embodiments are also contemplated wherein the counter electrode 4 may instead comprise an electrically conductive mesh. Such an approach has been demonstrated to work in principle although the mesh electrode can generate shadows which can complicate the automated identification of colonies. For this reason a transparent electrode having a transparent conductive coating or layer is particularly of interest.

According to embodiments which are of particular interest a transparent (or translucent) support plate or substrate may be provided which may be coated with a transparent (or translucent) conductive layer. The support plate or substrate may comprise a transparent or translucent glass plate which may coated with a transparent or translucent conductive layer on an upper surface of the glass support plate. It will be apparent, therefore, that the transparent or translucent conductive coating or layer will then be direct contact with the bottom of a petri dish 4 or other container. According to various embodiments the support plate or substrate may, for example, be coated with an indium-tin oxide ("ITO") layer. Coating the support plate or substrate with an indium-tin oxide layer is beneficial since the indium-tin oxide layer will have a significant conductivity and will also have sufficient mechanical strength for this application.

Figure 2:
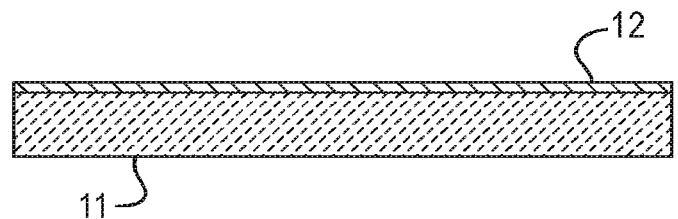
FIG. 2 shows a schematic of an embodiment wherein a counter electrode is provided comprising a transparent conductive indium-tin oxide layer which is deposited upon a glass support plate.

FIG. 2 shows a glass support plate 11 according to an embodiment which was fabricated. The glass support plate 11 was of optical grade and the top and bottom surfaces of the glass support plate 11 were polished. An indium-tin oxide layer 12 was then deposited onto the glass support plate 11 using a Physical Vapor Deposition ("PVD") process so that a layer of optically transparent indium-tin oxide having a thickness of about 1-2 μm was deposited onto the upper surface of the glass support plate 11.

The indium-tin oxide layer 12 is optically transparent and has sufficient transmission so as to enable bacterial colonies which may be present on a culture or growth medium such as agar located within a petri dish 4 or other container to be illuminated. The petri dish 4 may be placed in use on top of the glass support plate 11. The petri dish 4 or other container may be illuminated from below so that light passes in turn through the support plate 11, through the transparent layer 12 and then passes through the petri dish 4 in order to illuminate the culture or growth medium and any colonies growing on the culture or growth medium. Illuminating the petri dish 4 from below is particularly beneficial as it allows colony boundaries to be more easily determined and thus identified.

Figure 3:
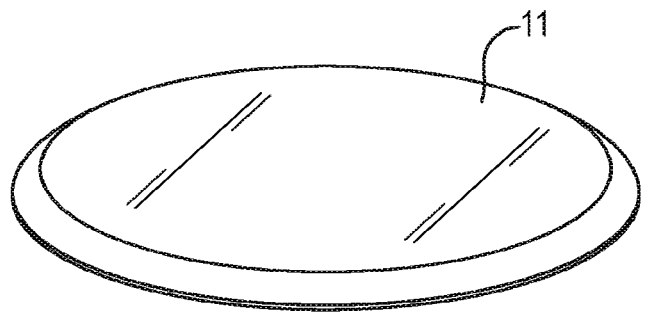
FIG. 3 shows in greater detail a circular glass support plate which may be coated with a transparent conductive layer in order to form a transparent counter electrode according to an embodiment.

FIG. 3 shows a glass support plate 11 according to an embodiment wherein the glass support plate 11 is arranged to have a 45° angled or bevelled edge. The angled or bevelled edge facilitates electrical contact at the side with the upper transparent conductive electrode 12 such as a layer of indium-tin oxide 12.

Figure 4:
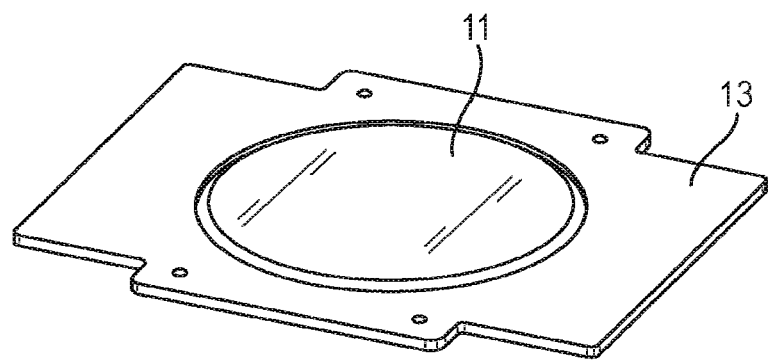
FIG. 4 shows a glass support plate located in a metal holder according to an embodiment.

As shown in FIG. 4, a metal plate 13 may be placed onto the glass support plate 11 and may be secured to a light box using springs. The edge of the opening in the metal plate 13 may be arranged so as to connect to the angled edge of the glass support plate 11 thereby ensuring that a reliable electrical contact is made between the metal plate 13 and the conductive electrode layer 12 on the upper surface of the glass support plate 11. The metal plate 13 also enables the glass support plate 11 to be precisely located or positioned.

Figure 5:
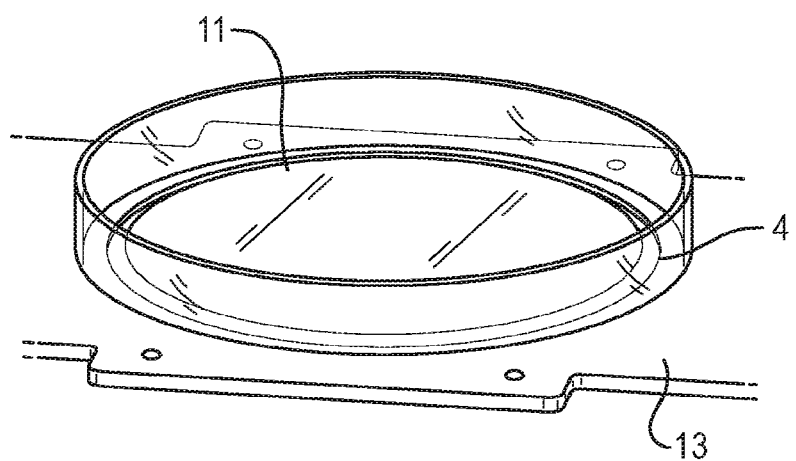
FIG. 5 shows a petri dish resting on a transparent counter electrode assembly according to an embodiment.

FIG. 5 shows an embodiment wherein a petri dish 4 or other container is located on a transparent conductive counter electrode comprising a glass support plate 11 having an upper conductive electrode layer 12. The petri dish 4 or other container may be fabricated from glass or plastic and hence is an insulator.

After one or more colonies which have grown on the culture or growth medium in the petri dish 4 or other container have been optically identified by, for example, the camera system 3 then the sampling head or REIMS probe 2 may then be moved so that the tip 5 of the REIMS sampling probe 2 comes into direct contact with the colony mass with the height being determined by, for example, using a capacitive liquid level sensor located in the robotic arm of the robotic system 1.

According to various embodiments the RF generator 6 may be energised for a short period of time (e.g. a pulse of 1 s) with the result that electrical energy is capacitively coupled into the sample in close proximity to tip 5 of the REIMS sampling probe 2. The result of the applied RF voltage is a rapid evaporation of the sample to form an aerosol which may then be aspirated into a vacuum chamber of the mass spectrometer 7 via a tube 8. The aerosol comprises analyte which may be ionised by, for example, an ion source located within a vacuum chamber of the mass spectrometer 7 with the result that analyte ions are then mass analysed by the mass spectrometer 7.

Figure 6:
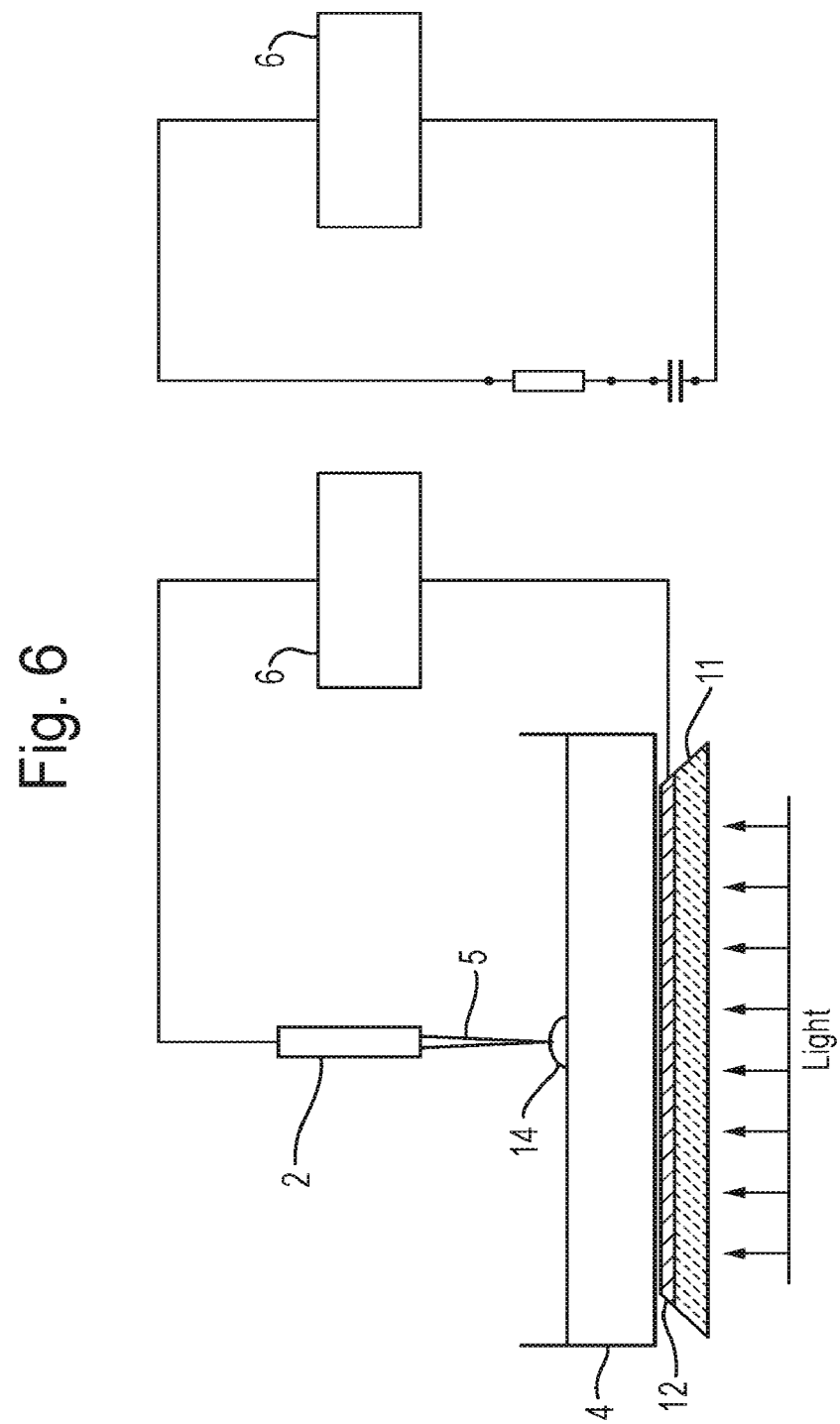
FIG. 6 shows a transparent counter electrode according to an embodiment located below a petri dish which contains a culture or growth medium and a microorganism colony which has been cultured on the culture or growth medium together with a simplified equivalent electrical circuit, wherein the colony may be illuminated from below the petri dish in order to aid microorganism identification and wherein a REIMS probe may be used to sample and analyse the microorganism colony.

FIG. 6 shows an embodiment showing a glass support plate 11 having an upper conductive layer 12. The glass support plate 11 and the conductive layer 12 may be both transparent (or at least translucent) and enable light from a light source (not shown) to pass through the glass support plate 11, the conductive layer 12 and the base of a petri dish 4 or other container located on the upper surface of the glass support plate 11 (and hence in direct contact with the conductive layer 12).

A REIMS sampling probe 2 comprising a tubular sampling head with a sampling tip 5 is shown. The tip 5 of the REIMS sampling probe 2 is in direct contact with a colony 14 on the surface of a culture or growth medium located in the petri dish 4 or other container. The REIMS sampling probe 2 and the upper conductive layer 12 of the glass support plate 11 are shown to be in electrical contact with an RF electrosurgical generator 6.

FIG. 6 also shows a simplified equivalent electrical circuit of the overall system. Current is arranged to pass through resistive layers (e.g. the colony and the agar culture or growth medium) and also through capacitive layers (e.g. the interface between the agar and the petri dish 4 and the interface between the petri dish 4 and the indium-tin oxide or other conductive layer 12). The result of capacitively coupling electrical energy into the sample is the generation of an aerosol comprising analytes which are subsequently mass analysed by a mass spectrometer 7.

Figure 7:
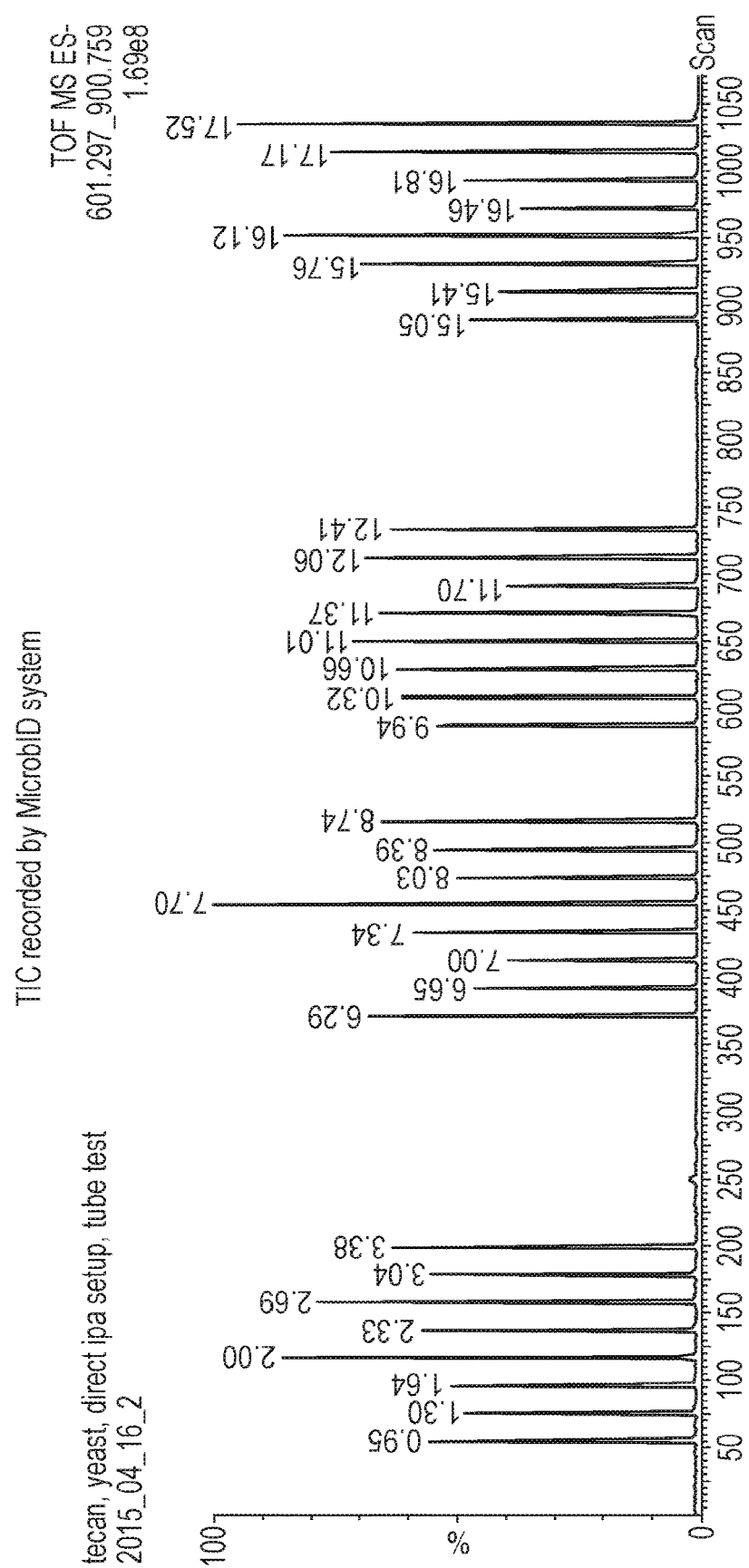
FIG. 7 shows a total ion current ("TIC") obtained by analysing a sample according to an embodiment.

FIG. 7 shows a sample total ion current TIC which was obtained when a yeast colony was mass analysed according to an embodiment as described above wherein a REIMS sampling probe 2 was used to sample a yeast colony on a culture or growth medium. A high signal intensity was obtained and the signal was obtained for the duration of the applied RF voltage pulse.

Figure 8:
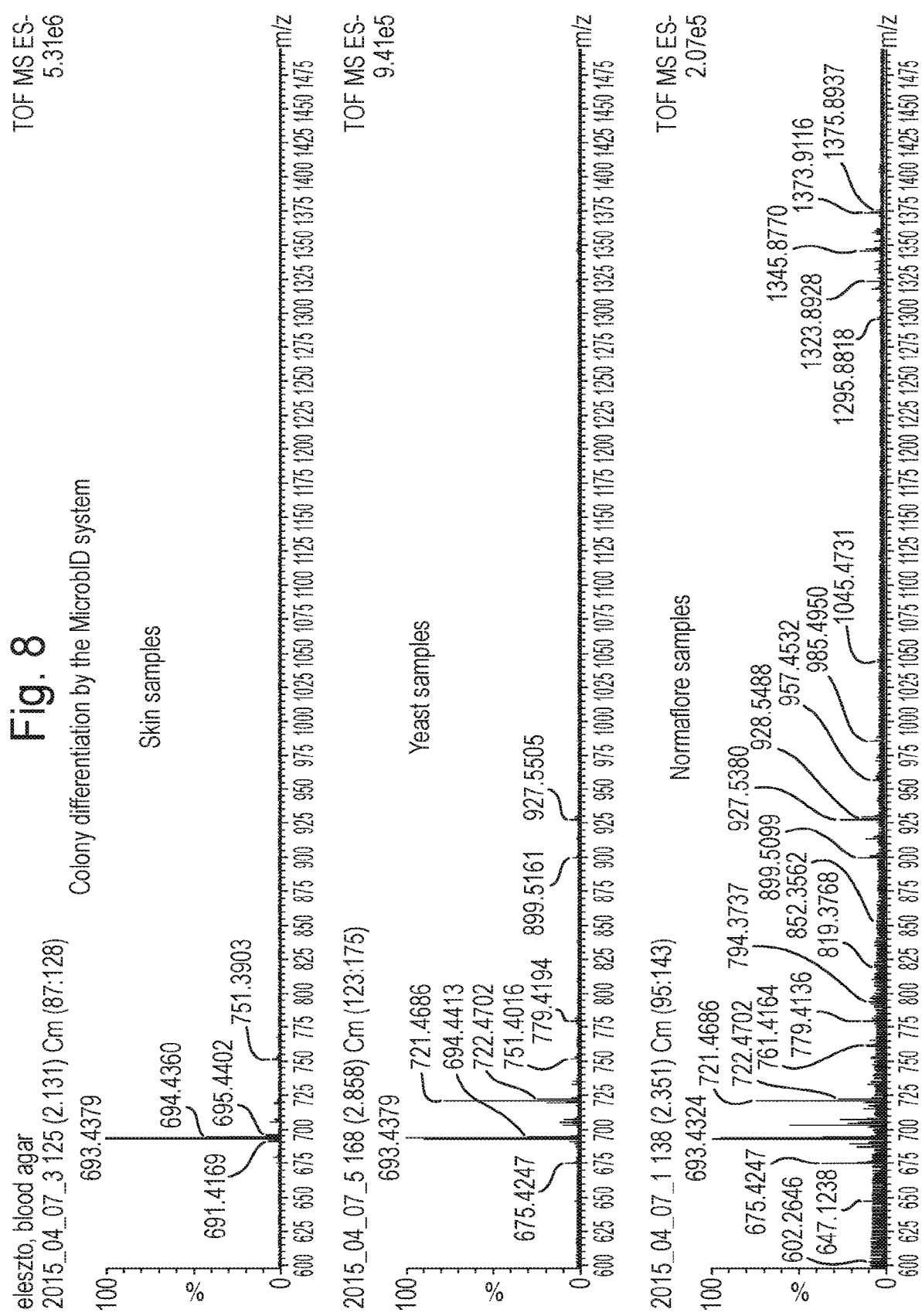
FIG. 8 shows three mass spectra which were obtained by analysing samples using the disclosed REIMS apparatus according to various embodiments and illustrates the ability of the disclosed REIMS apparatus to be able to differentiate between different types of colonies.

FIG. 8 shows three mass spectra relating to skin samples, yeast samples and normaflore samples wherein the samples were provided on a culture or growth medium and were obtained using a REIMS sampling probe 2 as discussed above. It is apparent from FIG. 8 that a high signal to noise ("S/N") ratio was obtained and that the different mass spectra enabled different colonies to be identified. The mass spectral peak at mass to charge ratio of 693.43 corresponds to a lipid which is common to all three samples. The different mass spectral peaks correspond predominantly to the colony being analysed with the agar culture or growth medium having an insignificant impact upon the resulting mass spectra.

It is apparent, therefore, that the REIMS sampling probe 2 according to various embodiments is able to identify various different biological substances on an agar substrate without needing to scrap sample from the agar substrate.

Various further embodiments are also contemplated. According to an embodiment the method may be utilised with micro-REIMS imaging experiments wherein, for example, a sample may be microtome sectioned and then a thin slice may be mounted on to a glass slide.

The method may also be used with simultaneous spectroscopy and rapid evaporation ionisation mass spectrometry imaging.

According to other embodiments the support plate 11 may be fabricated from materials other than glass such as a plastic such as polycarbonate, poly(methyl)methacrylate or Plexiglas®. Alternatively, the support plate 11 may be fabricated from quartz or another transparent insulator material.

It will also be understood that it is not essential that the support plate 11 is totally optically transparent. For example, the support plate 11 may be fabricated from an opaque, translucent or semi-translucent material.

It is also not essential that the conductive layer 12 provided on the support plate 11 comprises indium-tin oxide. For example, other embodiments are contemplated wherein the conductive layer 12 may comprise other transparent conductive oxides such as aluminum-doped zinc oxide ("AZO"), indium-doped cadmium oxide, aluminum-doped zinc oxide ("AZO"), gallium-doped zinc oxide ("GZO") or indium-doped zinc oxide ("IZO").

According to other embodiments the conductive layer 12 on the surface of the support plate 11 may comprise a thin translucent or transparent metallic layer.

Alternatively, the translucent or transparent layer 12 on the surface of the support plate 11 may comprise a carbon nanotube conductive coating, a graphene film or silver nanowires covered with graphene.

The transparent or translucent layer 12 on the surface of the support plate 11 may alternatively comprise a conductive polymeric layer such as polyaniline or poly(3,4-ethylenedi-oxythiophene):poly(styrenesulfonate) ("PEDOT:PSS") composite.

It is also contemplated that the counter electrode 9,12 may comprise a conductive plastic foil. The transparent supporting plate 11 and the conductive plastic foil may be assembled using a fixture that holds them together.

Other embodiments are contemplated wherein the culture or growth medium may comprise a liquid medium, a cell growth medium such as but not limited to DME (Dulbecco's Modified Eagle's medium), a modified DME medium (e.g. glucose or glutamine free), RPMI (Roswell Park Memorial Institute medium), MEM (Minimum Essential Medium), IMDM (Iscove's Modified Dulbecco's Medium) or another liquid growth medium.

The sample may be spun down using a centrifuge to form a pellet and the supernate may be discarded or used for subsequent analysis.

The sample or pellet may be smeared onto a glass slide or other insulating surface, or may be anlaysed in situ.

Although the present invention has been described with reference to preferred embodiments, it will be understood by those skilled in the art that various changes in form and detail may be made without departing from the scope of the invention as set forth in the accompanying claims.

The invention claimed is:

1. A method of analysis comprising:
locating a sample on a first electrode;
passing light or photons through said first electrode in order to illuminate, image or analyse said sample;
contacting said sample with a second electrode; and
applying an AC or RF voltage to said first and second electrodes in order to generate an aerosol from said sample.

2. A method as claimed in claim 1, wherein the step of providing a sample on said first electrode comprises providing said sample in a container, a petri dish, a vial or a microtitre or microwell plate.

3. A method as claimed in claim 1, wherein said sample comprises a biological, bacterial, fungal or yeast sample or a cell line which has been cultured on to or within a culture or growth medium, wherein said culture or growth medium comprises a solid or liquid culture or growth medium.

4. A method as claimed in claim 1, wherein the step of applying said AC or RF voltage to said first and second electrodes is such that electrical energy is predominantly capacitively coupled into said sample.

5. A method as claimed in claim 1, wherein said first electrode comprises a mesh electrode.

6. A method as claimed in claim 1, wherein said first electrode comprises a substrate which is substantially optically transparent or optically translucent.

7. A method as claimed in claim 6, wherein said substrate further comprises a conductive layer or a conductive coating.

8. A method as claimed in claim 7, wherein said conductive layer or said conductive coating is substantially optically transparent or optically translucent.

9. A method as claimed in claim 1, wherein the step of applying said AC or RF voltage to said first and second electrodes causes electrical energy to be transferred into said sample so as to cause said aerosol to be generated.

10. A method as claimed in claim 1, further comprising directing at least some of the aerosol into a vacuum chamber of a mass spectrometer and ionising at least some the aerosol within a or the vacuum chamber of the mass spectrometer so as to generate a plurality of analyte ions.

11. A method as claimed in claim 10, further comprising mass analysing said analyte ions.

12. A method as claimed in claim 10, further comprising spectroscopically imaging or analysing said sample.

13. A method as claimed in claim 12, wherein the step of spectroscopically imaging or analysing said sample further comprises spectroscopically imaging or analysing said sample at substantially the same time as obtaining mass spectral data corresponding to one or more locations on or in said sample.

14. A method as claimed in claim 12, wherein the step of spectroscopically imaging or analysing said sample comprises subjecting said sample to Raman spectroscopy and/or to infra-red ("IR") spectroscopy.

15. A method as claimed in claim 13, further comprising using said obtained mass spectral data to identify one or more biological substances, one or more bacterial strains, one or more fungal strains, one or more yeast strains or one or more cell lines located at one or more locations on or in said sample.

16. A method of rapid evaporation ionization mass spectrometry ("REIMS") comprising a method as claimed in claim 1.

17. An apparatus comprising:
a first electrode;
a first device arranged for passing light or photons through said first electrode in order to illuminate, image or analyse, in use, a sample located on said first electrode;
a second electrode for contacting said sample; and
a second device for applying an AC or RF voltage to said first and second electrodes in order to generate an aerosol from said sample.

18. An apparatus as claimed in claim 17, wherein said first electrode comprises a substrate which is substantially optically transparent or optically translucent.

19. An apparatus as claimed in claim 17, wherein said first electrode comprises a mesh electrode.

20. An apparatus as claimed in claim 18, wherein said substrate further comprises a conductive layer or a conductive coating.

* * * * *